US008239023B2

(12) United States Patent
Shuros et al.

(10) Patent No.: US 8,239,023 B2
(45) Date of Patent: *Aug. 7, 2012

(54) INTEGRATED CARDIAC RHYTHM MANAGEMENT SYSTEM WITH HEART VALVE

(75) Inventors: Allan C. Shuros, St. Paul, MN (US); Michael J. Kane, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 286 days.

This patent is subject to a terminal disclaimer.

(21) Appl. No.: 12/645,934

(22) Filed: Dec. 23, 2009

(65) Prior Publication Data

US 2010/0100144 A1   Apr. 22, 2010

Related U.S. Application Data

(63) Continuation of application No. 11/466,974, filed on Aug. 24, 2006, now Pat. No. 7,643,879.

(51) Int. Cl.
*A61N 1/00* (2006.01)
(52) U.S. Cl. ............ 607/18; 623/2.1; 600/515; 600/513
(58) Field of Classification Search ................ 607/4–28; 600/508–521; 623/2.1
See application file for complete search history.

(56) References Cited

U.S. PATENT DOCUMENTS

| 4,671,295 | A | 6/1987 | Abrams et al. |
| 4,733,669 | A | 3/1988 | Segal |
| 4,769,032 | A | 9/1988 | Steinberg |
| 4,947,852 | A | 8/1990 | Nassi et al. |
| 5,188,106 | A | 2/1993 | Nappholz et al. |
| 5,192,313 | A | 3/1993 | Budd et al. |
| 5,316,001 | A | 5/1994 | Ferek et al. |
| 5,480,412 | A | 1/1996 | Mouchawar et al. |
| 5,487,760 | A | 1/1996 | Villafana |
| 5,564,434 | A | 10/1996 | Halperin et al. |
| 5,944,751 | A | 8/1999 | Laub |
| 6,053,873 | A | 4/2000 | Govari et al. |
| 6,261,233 | B1 | 7/2001 | Kantorovich |
| 6,277,078 | B1 | 8/2001 | Porat et al. |
| 6,287,253 | B1 | 9/2001 | Ortega et al. |
| 6,308,715 | B1 | 10/2001 | Weissman et al. |

(Continued)

FOREIGN PATENT DOCUMENTS

WO    WO-9926530 A1    6/1999

(Continued)

OTHER PUBLICATIONS

"U.S. Appl. No. 11/250,928, Final Office Action mailed Jan. 3, 2011", 27 pgs.

(Continued)

*Primary Examiner* — Scott Getzow
(74) *Attorney, Agent, or Firm* — Schwegman, Lundberg & Woessner, P.A.

(57) ABSTRACT

Systems and methods using a heart valve and an implantable medical device, such as for event detection and optimization of cardiac output. The cardiac management system includes a heart valve, having a physiological sensor. The physiological sensor is adapted to measure at least one of an intrinsic electrical cardiac parameter, a hemodynamic parameter or the like. The system further includes an implantable electronics unit, such as a cardiac rhythm management unit, coupled to the physiological sensor of the heart valve to receive physiological information. The electronics unit is adapted to use the received physiological information to control delivery of an electrical output to the subject.

20 Claims, 12 Drawing Sheets

U.S. PATENT DOCUMENTS

| | | |
|---|---|---|
| 6,309,350 B1 | 10/2001 | VanTassel et al. |
| 6,361,554 B1 | 3/2002 | Brisken |
| 6,387,116 B1 | 5/2002 | McKenzie et al. |
| 6,398,734 B1 | 6/2002 | Cimochowski et al. |
| 6,409,674 B1 | 6/2002 | Brockway et al. |
| 6,431,175 B1 | 8/2002 | Penner et al. |
| 6,440,059 B1 | 8/2002 | Haas et al. |
| 6,442,413 B1 | 8/2002 | Silver |
| 6,454,720 B1 | 9/2002 | Clerc et al. |
| 6,475,170 B1 | 11/2002 | Doron et al. |
| 6,486,588 B2 | 11/2002 | Doron et al. |
| 6,504,286 B1 | 1/2003 | Porat et al. |
| 6,524,333 B1 | 2/2003 | Claren et al. |
| 6,628,990 B1 | 9/2003 | Habib et al. |
| 6,636,769 B2 | 10/2003 | Govari et al. |
| 6,638,231 B2 | 10/2003 | Govari et al. |
| 6,645,143 B2 | 11/2003 | VanTassel et al. |
| 6,652,464 B2 | 11/2003 | Schwartz et al. |
| 6,658,300 B2 | 12/2003 | Govari et al. |
| 6,659,959 B2 | 12/2003 | Brockway et al. |
| 6,673,104 B2 | 1/2004 | Barry |
| 6,682,480 B1 | 1/2004 | Habib et al. |
| 6,692,446 B2 | 2/2004 | Hoek |
| 6,702,847 B2 | 3/2004 | DiCarlo |
| 6,726,677 B1 | 4/2004 | Flaherty et al. |
| 6,743,180 B1 | 6/2004 | Van Bockel |
| 6,746,404 B2 | 6/2004 | Schwartz |
| 6,755,853 B2 | 6/2004 | McKenzie et al. |
| 6,783,499 B2 | 8/2004 | Schwartz |
| 6,802,811 B1 | 10/2004 | Slepian |
| 6,802,857 B1 | 10/2004 | Walsh et al. |
| 6,895,265 B2 | 5/2005 | Silver |
| 6,918,873 B1 | 7/2005 | Millar et al. |
| 6,953,438 B2 | 10/2005 | Milo |
| 6,953,476 B1 | 10/2005 | Shalev |
| 7,006,858 B2 | 2/2006 | Silver et al. |
| 7,097,618 B1 | 8/2006 | Benditt et al. |
| 7,209,786 B2 | 4/2007 | Brockway et al. |
| 7,274,961 B1 | 9/2007 | Kroll et al. |
| 7,643,879 B2 | 1/2010 | Shuros et al. |
| 2001/0000792 A1 | 5/2001 | Bowman |
| 2001/0016690 A1 | 8/2001 | Chio |
| 2001/0025151 A1 | 9/2001 | Kimball et al. |
| 2002/0072656 A1 | 6/2002 | Vantassel et al. |
| 2002/0120204 A1 | 8/2002 | Pfeiffer et al. |
| 2002/0128561 A1 | 9/2002 | Rheinhardt et al. |
| 2002/0138009 A1 | 9/2002 | Brockway et al. |
| 2002/0173724 A1 | 11/2002 | Dorando et al. |
| 2002/0177783 A1 | 11/2002 | Khalil |
| 2002/0183629 A1 | 12/2002 | Fitz |
| 2002/0183632 A1 | 12/2002 | Krivitski et al. |
| 2003/0055353 A1 | 3/2003 | Webber et al. |
| 2003/0069608 A1 | 4/2003 | Sweeney |
| 2003/0120162 A1 | 6/2003 | Bowman |
| 2003/0158491 A1 | 8/2003 | Krivitski et al. |
| 2003/0225336 A1 | 12/2003 | Callister et al. |
| 2004/0034306 A1 | 2/2004 | Seward |
| 2004/0054293 A1 | 3/2004 | Krivitski et al. |
| 2004/0127958 A1 | 7/2004 | Mazar et al. |
| 2004/0176672 A1 | 9/2004 | Silver et al. |
| 2004/0176810 A1 | 9/2004 | Stadler et al. |
| 2004/0181158 A1 | 9/2004 | Bowman |
| 2004/0193023 A1 | 9/2004 | Mardirossian |
| 2004/0215070 A1 | 10/2004 | Letort et al. |
| 2004/0220484 A1 | 11/2004 | Steuer et al. |
| 2004/0254483 A1 | 12/2004 | Zdeblick et al. |
| 2005/0004478 A1 | 1/2005 | Fitz |
| 2005/0070807 A1 | 3/2005 | Marks et al. |
| 2005/0080346 A1 | 4/2005 | Gianchandani et al. |
| 2005/0102026 A1 | 5/2005 | Turner et al. |
| 2005/0240110 A1 | 10/2005 | Liu et al. |
| 2005/0267378 A1 | 12/2005 | Pfeiffer et al. |
| 2005/0267379 A1 | 12/2005 | Pfeiffer et al. |
| 2005/0273014 A1 | 12/2005 | Gianchandani et al. |
| 2006/0058609 A1 | 3/2006 | Olstad |
| 2007/0049974 A1 | 3/2007 | Li et al. |
| 2007/0088214 A1 | 4/2007 | Shuros et al. |
| 2007/0225802 A1 | 9/2007 | Forsell |
| 2008/0051838 A1 | 2/2008 | Shuros et al. |
| 2008/0306359 A1 | 12/2008 | Zdeblick et al. |

FOREIGN PATENT DOCUMENTS

| | | |
|---|---|---|
| WO | WO-0032092 A1 | 6/2000 |
| WO | WO-02064019 A2 | 8/2002 |
| WO | WO-2005046467 A1 | 5/2005 |
| WO | WO-2008024180 A1 | 2/2008 |

OTHER PUBLICATIONS

"U.S. Appl. No. 11/250,928, Final Office Action mailed Mar. 12, 2010", 20 pgs.

"U.S. Appl. No. 11/250,928, Non-Final Office Action mailed Sep. 1, 2010", 21 pgs.

"U.S. Appl. No. 11/250,928, Response filed Aug. 11, 2010 to Final Office Action mailed Mar. 12, 2010", 11 pgs.

"U.S. Appl. No. 11/250,928, Response filed Oct. 22, 2010 to Non-Final Office Action mailed Sep. 1, 2010", 12 pgs.

"U.S. Appl. No. 11/250,928, Examiner Interview Summary mailed Dec. 18, 2009", 4 pgs.

"U.S. Appl. No. 11/250,928, Final Office Action mailed Jan. 5, 2009", 23 pgs.

"U.S. Appl. No. 11/250,928, Non-Final Office Action mailed Jun. 2, 2008", 18 pgs.

"U.S. Appl. No. 11/250,928, Non-Final Office Action mailed Sep. 18, 2009", 22 pgs.

"U.S. Appl. No. 11/250,928, Response filed Jul. 6, 2009 to Final Office Action mailed Jan. 5, 2009", 14 pgs.

"U.S. Appl. No. 11/250,928, Response filed Oct. 2, 2008 to Non-Final Office Action mailed Jun. 2, 2008", 13 pgs.

"U.S. Appl. No. 11/250,928, Response filed Dec. 12, 2009 to Non Final Office Action mailed Sep. 18, 2009", 15 pgs.

"U.S. Appl. No. 11/466,974, Final Office Action mailed Jan. 30, 2009", 9 pgs.

"U.S. Appl. No. 11/466,974, Non-Final Office Action mailed Aug. 15, 2008", 7 pgs.

"U.S. Appl. No. 11/466,974, Notice of Allowance mailed Aug. 24, 2009", 4 pgs.

"U.S. Appl. No. 11/466,974, Response filed May 28, 2009 to Final Office Action mailed Jan. 28, 2009", 16 pgs.

"U.S. Appl. No. 11/466,974, Response filed Nov. 17, 2008 to Non Final Office Action mailed Aug. 15, 2008", 21 pgs.

"Chemical Species Gas Sensors", http://www.grc.nasa.gov/WWW/chemsensors/, (observed May 19, 2006), 6 pgs.

"PCT Application No. PCT/US2007/017119, International Search Report mailed Dec. 5, 2007", 3 pgs.

"PCT Application No. PCT/US2007/017119, Written Opinion mailed Dec. 5, 2007", 7 pgs.

Berger, R. M. F., et al., "Pulmonary Arterial Wall Distensibility Assessed by Intravascular Ultrasound in Children With Congenital Heart Disease: An Inducator for Pulmonary Vascular Disease", *Chest*, 122(2), (Aug. 2002), 549-557.

Hauser, R. G., "Techniques for Improving Cardiac Performance With Implantable Devices", *Pacing and Clinical Electrophysiology*, 7(6)(Part II), (Nov. 1984), 1234-1239.

Kane, et al., "Implantable Medical Device With Chemical Sensor and Related Methods", *U.S. Appl. No. 11/383,933, filed May 17, 2006*, 68 pgs.

Kane, et al., "Implantable Medical Device With Chemical Sensor and Related Methods", *U.S. Appl. No. 11/383,926, filed May 17, 2006*, 66 pgs.

Lanning, C., et al., "Development and Validation of Implantable Sensors for Monitoring Function of Prosthetic Heart Valves: in vitro Studies", *Medical & Biological Engineering & Computing*, 41(4), (Jul. 2003), 416-424.

Martin, R., et al., "An Ultrasonic Catheter for Intravascular Measurement of Blood Flow: Technical Details", *IEEE Transactions on Sonics and Ultrasonics vol. SU-27*, (1980), 277-286.

Mussivand, T., et al., "A Remotely Controlled and Powered Artificial Heart Pump", *Artificial Organs*, 20(12), (Dec. 1996), 1314-1319.

Shuros, A., et al., "Implantable Physiologic Monitoring System", *U.S. Appl. No. 11/250,928, filed Oct. 14, 2005*, 30 pgs.

INTEGRATED CARDIAC RHYTHM MANAGEMENT SYSTEM WITH HEART VALVE

CROSS REFERENCE TO RELATED APPLICATIONS

This is a Continuation of U.S. application Ser. No. 11/466,974, filed on Aug. 24, 2006, now issued as U.S. Pat. No. 7,643,879, which is herein incorporated by reference.

TECHNICAL FIELD

Event detection and therapy with biomedical devices and in particular event detection and therapy using sensors coupled with a heart valve.

BACKGROUND

The body includes a plurality of organs and systems that perform functions necessary for maintaining the health of a person. The circulatory system is one example of a system that includes the heart organ as its centerpiece. Other body systems include the respiratory system, digestive system, endocrine system, nervous system or the like. The organs of these systems provide a variety of physiological parameters useful for observing the normal and abnormal behaviors of the body. Observation of these parameters and recognition of potential normal and abnormal events through observation allows effective diagnosis or treatment of diseases, conditions or the like. The complexity of the various systems of the body provide multiple parameters that, when observed, provide insight regarding the onset of a condition or disease. Measuring each of these parameters and correctly identifying when measurements indicate a condition is difficult. Identifying a condition becomes even more difficult when some measurements indicate the onset or existence of a condition or disease while others do not.

One example of a body system is the circulatory system. The heart is the central organ for the circulatory system and includes an electromechanical system performing two major pumping functions. The left portions of the heart draw oxygenated blood from the lungs and pump it to the organs of the body to provide the organs with oxygen. The right portions of the heart draw deoxygenated blood from the organs and pump it into the lungs where the blood is oxygenated. The pumping functions are accomplished by contractions of the heart. An increase in the body's metabolic need for oxygen is satisfied primarily by a higher frequency of the contractions, i.e., a higher heart rate, along with changes in stroke volume.

Measurements of the various electrical and mechanical functions of the heart provide a variety of physiological parameters that can indicate the onset of a condition, for instance, heart failure, arrhythmia (fibrillation, tachycardia, bradycardia), ischemia, or the like. These physiological parameters include, for example, electrocardiac characteristics, heart sounds (e.g., S3 amplitude), DC impedance near the lungs, heart rate, respiration rate, weight, intracardiac pressure, blood flow, blood velocity, temperature, chemical presence and concentration or the like. At least some of these parameters may indicate the onset or change of a condition and thereby provide an alert that therapy or therapy adjustment is needed, such as defibrillation, change in pacing schema or the like. It is difficult, however, to determine when an event is beginning when only some measurements for these parameters indicate the onset of a condition.

In some examples, clinicians set measured parameter thresholds in implantable medical devices, such as pacemakers, defibrillators, cardiac resynchronization devices, or the like. Many clinicians adopt a conservative approach geared toward applying therapy even when therapy may not be needed.

Therapy is thereby provided when at least one or more of the measurements for a parameter are above the set threshold—even when the measurements for other parameters indicate there is not an event. False positives, non-events that include measurements above at least some thresholds, thereby initiate treatment. In some circumstances, such as defibrillation shock therapy, the user of the implantable medical device receives painful and unnecessary treatment in response to such a false positive. The issues described above, with regard to cardiac therapy, such as setting conservative thresholds or the like, extend to other medical devices associated with the other organs and systems of the body.

Further, information about when many conditions begin may involve the left ventricle or left atrium. It is difficult to position sensors within the left side of the heart. The ability to precisely measure physiological parameters of the left side of the heart is thereby limited. Further still, because of the convoluted vasculature it is difficult to position electrodes for defibrillation and pacing therapy within the left side of the heart.

The present inventors have recognized that event detection systems and methods that address the above issues are needed. The present inventors have also recognized that what is further needed are implantable event detection systems capable of sensing multiple physiological parameters and providing increased specificity for delivery of therapy, such as in difficult to reach locations of the heart.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1A:
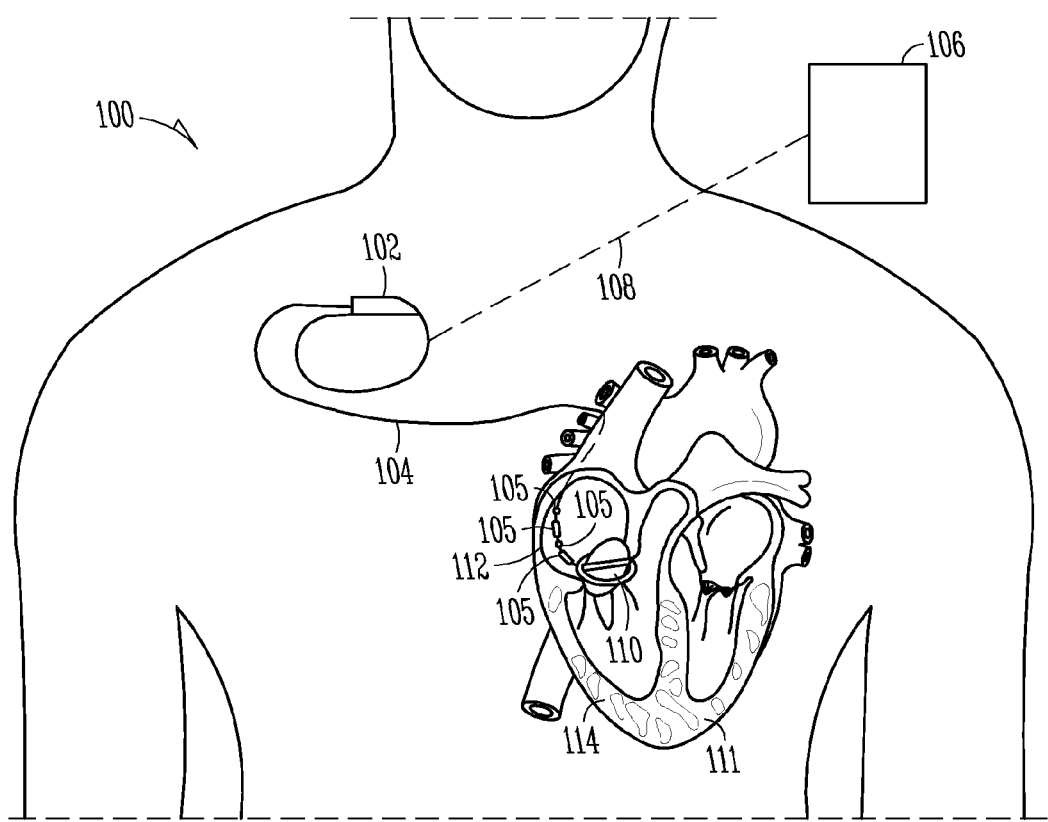
FIG. 1A is a schematic diagram showing one example of a cardiac management system including a replacement tricuspid heart valve.

FIGS. 1A, B are schematic diagrams showing examples of portions of a cardiac management system 100 including an implantable medical device 102, a lead system 104, an external system 106, and a wireless telemetry link 108. In one example, the implantable medical device 102 includes a cardiac function management device, such as a cardiac pacer, defibrillator, cardioverter, cardiac resynchronization devices, combinations of any two or more of the above, or the like for permanent or semi-permanent implantation. In another example, the external system 106 includes a wireless server system, such as the LATITUDE® system, a registered trademark of Cardiac Pacemakers, Inc. of St. Paul, Minn.

As shown in the examples of FIGS. 1A, B, the lead system 104 is coupled with a replacement heart valve 110. Optionally, the lead system 104 couples with the heart valve through the atrium 112 of the heart 111 similarly to some sensing and therapy leads. In another option, shown in FIG. 1A, the lead system 104 includes electrodes 105, such as pacing and/or defibrillation electrodes, operable to provide therapy to the heart at a variety of locations along the lead system 104. In yet another option, shown in FIG. 1B, the lead system 104 is coupled with the valve 110 extravascularly, for instance through the myocardium.

Figure 1B:
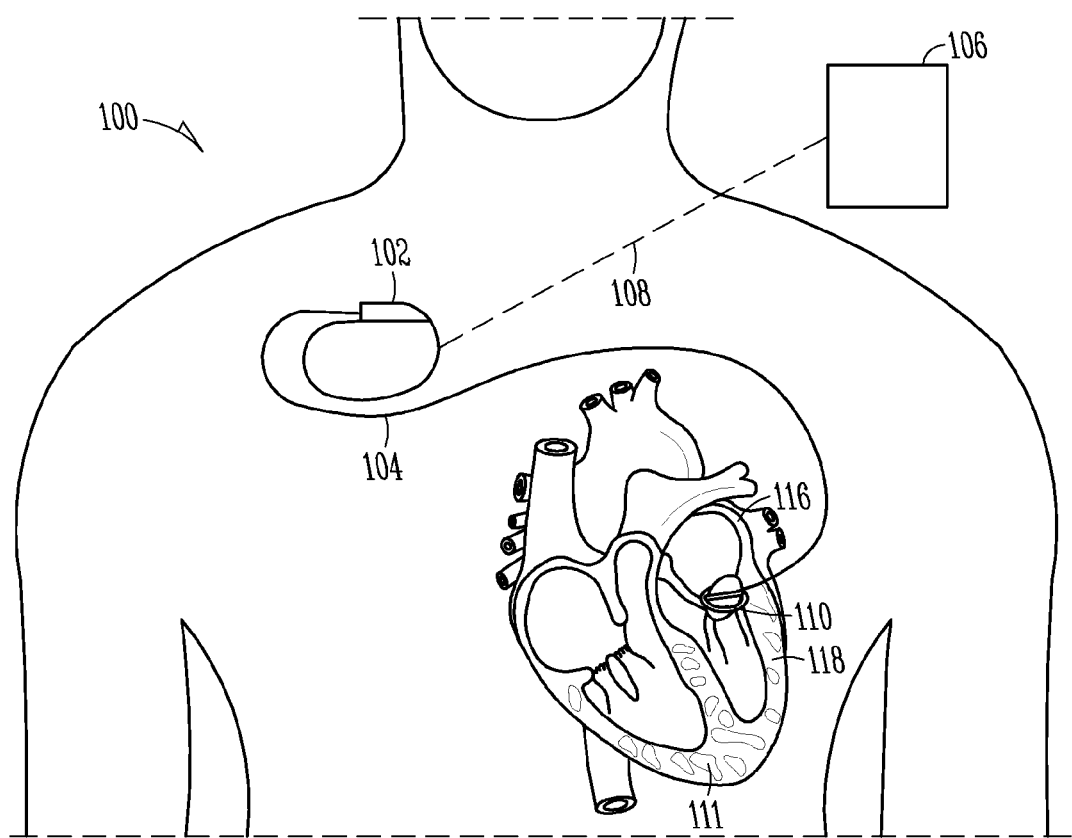
FIG. 1B is a schematic diagram showing one example of a cardiac management system including a replacement mitral heart valve.

In FIG. 1A, the replacement valve 110 is shown between the right atrium 112 and the right ventricle 114 in place of the tricuspid valve. In FIG. 1B, the replacement valve 110 is shown between left atrium 116 and the left ventricle 118 in place of the mitral valve. The heart valve 110 includes one or more sensors, including, but not limited to at least one of a hemodynamic sensor (e.g., valve deflection sensors, blood flow sensors, chemical sensors, temperature sensors, pressure sensors or the like) and one or more electrodes for cardiac sensing, pacing, defibrillation or the like, further described below. The sensors communicate with the implantable medical device 102 and provide information used by the implantable medical device 102, such as to apply and change, for instance, pacing therapy, defibrillation therapy, drug dispensing or the like.

Figure 1C:
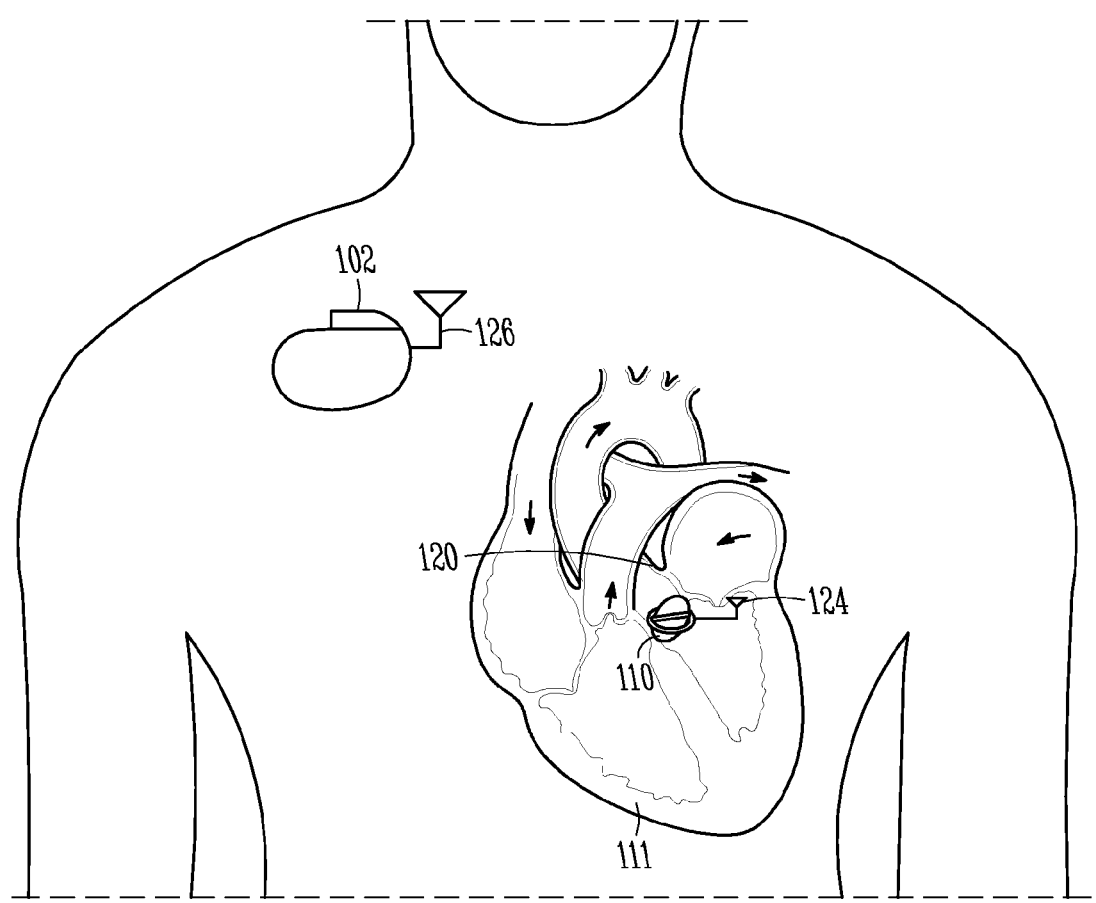
FIG. 1C is a schematic diagram showing one example of a cardiac management system including a replacement aortic heart valve.
Figure 1D:
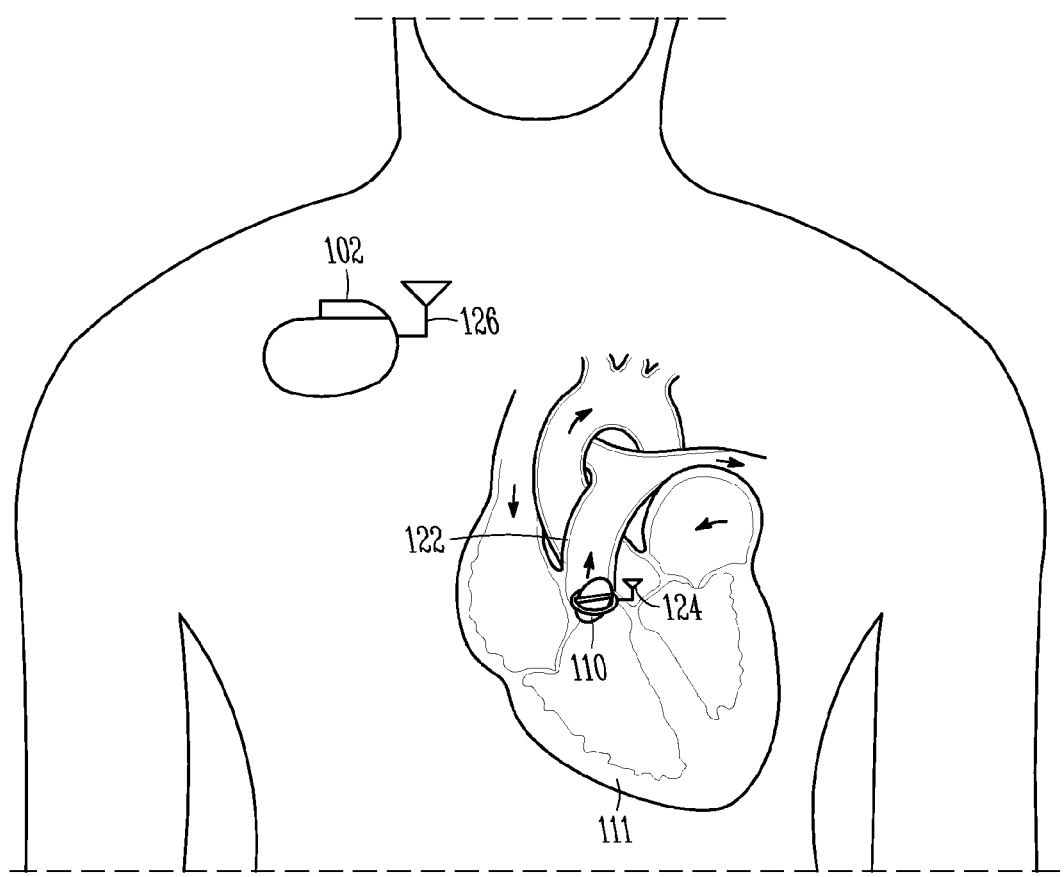
FIG. 1D is a schematic diagram showing one example of a cardiac management system including a replacement pulmonic heart valve.

FIGS. 1C, D are schematic diagrams showing another example of the heart valve 110. In FIG. 1C, the heart valve 110 is placed within the aorta 120 and replaces the aortic valve. In FIG. 1D, the heart valve is placed within the pulmonary artery 122 and replaces the pulmonic valve. As shown, in the examples of FIGS. 1C, D, the heart valve 110 is wirelessly coupled with the implantable medical device 102 through the use of a transceiver 124 (e.g., a transmitter, receiver, transmitter/receiver, or the like). The implantable medical device 102 similarly includes a transceiver 126. The transceivers 124, 126 communicate information from the valve 110 to the implantable medical device 102 such as for use by the implantable device 102 to apply and change, for instance, pacing and/or defibrillation therapy. In another example, the transceivers 124, 126 communicate an alert to the external system 106 (FIGS. 1A, B). Optionally, the transceivers 124, 126 use electromagnetic transmissions (e.g., RF) to communicate. In other examples, the transceivers 124, 126 use ultrasound, inductive coupling, optical transmission (e.g., infrared), electric field, the body as an electrical, optical or acoustic conductor or the like to communicate. In yet another example, the heart valves 110 shown in the aorta 120 and the pulmonary artery 122 are coupled to the implantable medical device 102 with a lead system similar to the lead system 104, described above. In still another example, the heart valves 110 shown in FIGS. 1A, B are wirelessly coupled with the implantable medical device 102, as described above. In an additional example, the heart 111 includes two or more implantable heart valves 110 (e.g., tricuspid and mitral, pulmonic and aortic, combinations of the same or the like).

Figure 2:
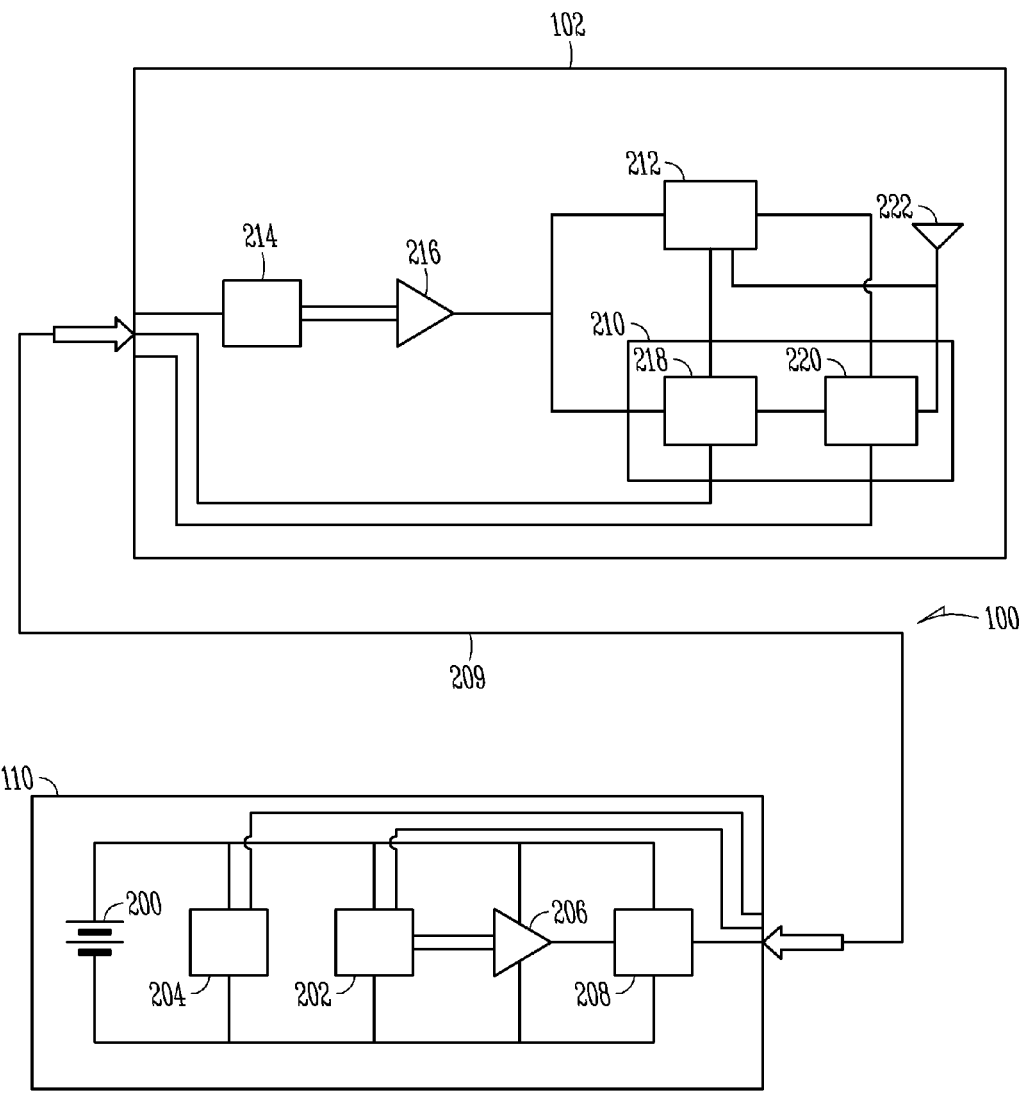
FIG. 2 is a schematic diagram showing one example of a cardiac management system with a heart valve.

FIG. 2 shows one example of the cardiac management system 100 including the implantable medical device 102 and the heart valve 110. As shown, the heart valve 110 includes a power source 200 and at least one sensor 202, such as an intrinsic cardiac sensor, hemodynamic parameter sensor or the like. In another example, the heart valve includes at least one electrode 204 adapted to provide sensing of intrinsic electrical cardiac or other parameters and/or therapy to the heart 111 (FIGS. 1A-D), such as pacing and/or defibrillation therapy. The electrode 204 is optionally constructed with, but not limited to, bio-compatible materials such as platinum, iridium, or the like. In yet another example, the heart valve 110 includes a signal processing circuit, for instance, a preamplifier 206 adapted to amplify the sensor measurements prior to transmitting the measurements to the implantable medical device 102. Optionally, the signal processing circuit includes an amplifier, filter, analog-to-digital converter and the like. The heart valve 110 includes, in still another example, a signal communications interface 208. The signal communications interface includes 208, but is not limited to a transceiver (such as the transceiver 124, described above), a socket for coupling with a lead assembly (such as the lead assembly 104, also described above) or the like, and facilitates communication of instructions and data between the heart valve 110 and the implantable medical device 102 along a communications link 209. The communications link 209 represents a flow of data (e.g., measurements, instructions or the like) between the heart valve 110 and the implantable medical device 102. For instance, the communications link 209 is at least one of a wired, wireless, optical, electromagnetic field coupling or the like between the devices that permits communication.

The implantable medical device 102 generally includes processor module 210 and a storage module 212. In one example, the implantable medical device 102 receives information from the heart valve 102 at a second signal communications interface 214. Similar to the signal communications interface 208, the second signal communications interface 214 of the device 102 includes, but is not limited to a transceiver, a socket for the lead assembly 104 or the like. Optionally, the implantable medical device 102 includes an amplifier 216 or other signal processing circuit coupled between the signal communications interface 208, the processor module 210 and the storage module 212. As shown in FIG. 2, the processor module 210 includes, in another example, a comparator module 218 and a therapy module 220. One or more of the processor module 210 (i.e., the module 210 generally or at least one of the therapy module 220, the comparator module 218 and the like) and the storage module 212 are coupled with a transceiver 222, in still another example. The transceiver facilitates communication with one or more external devices, such as external system 106.

In operation, the sensor 202 of the heart valve 110 measures at least one physiological parameter such as intrinsic cardiac electrical activity, one or more hemodynamic parameters, chemical composition of the blood, temperature, valve patency, valve functionality or the like. Optionally, the valve 110 includes multiple sensors 202, as described below, such as for measuring multiple physiological parameters. The measurement of the physiological parameter is sent through the signal processing circuit including the amplifier 206, in one example, and passed on to the signal communications interface 208. The signal communications interface 208, as described above, transmits the measurement (for instance, wirelessly, by the lead assembly 104 or the like) to the second signal communications interface 214 in the implantable medical device 102. In another example, the measurement is amplified by the amplifier 216 and sent to at least one of the storage module 212 and the comparator module 218. The measurement is compared against a specified threshold in the module 218, in yet another example. In one option, an alert is sent to the therapy module 220, for instance, if the measurement is above the specified threshold. In another option, an alert is sent to the therapy module 220 if the measurement is below the specified threshold. In still another example, the therapy module 220 sends a signal to the heart valve 110 and, in response, at least one electrode 204 at the valve 110 provides therapy (e.g., pacing, defibrillation or the like) to the heart 111 (FIGS. 1A-D). In yet another example, the therapy module 220 sends a signal to a separate lead assembly with pacing and/or defibrillation electrodes to provide therapy to the heart 111. In a further example, the therapy module 220 sends a signal to control dispensing of a drug into the patient according to the physiological parameter measurement. Where the measurement does not trigger the comparator module 218, optionally, an instruction is sent back to the heart valve 110 requesting another measurement. In another option, the heart valve 110 automatically measures the physiological parameter (e.g., at an interval, according to instructions from the implantable medical device, or the like).

In another example, the measurements retained in the storage module 212 are available through the transmitter 222 for use by, for instance, the external system 106 (FIGS. 1A, B). Similarly, in yet another example, the therapy module 220 is coupled with the transmitter 222, and optionally transmits to the external system 106 any therapy instructions sent to the heart valve 110.

Figure 3:
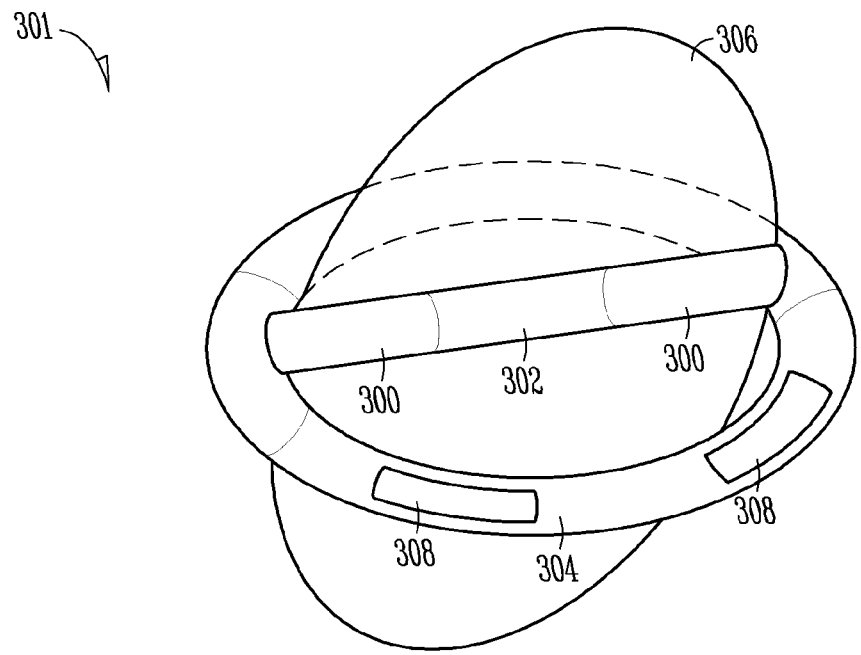
FIG. 3 is a perspective view of one example of a heart valve with a sensor for measuring at least a hemodynamic parameter.

FIG. 3 shows another example of the heart valve 301 including a sensor 300 for measuring at least one hemodynamic parameter, such as valve deflection, rate of change of valve deflection, blood velocity, blood flow, duration of valve opening or the like. Such parameters provide information about cardiac output, ejection fraction, contractility or the like and assist in indicating the onset of an event (e.g., tachycardia, defibrillation or the like) or change of an existing condition. As shown in FIG. 3, the sensor 300 is coupled between a strut 302 and a valve ring 304 of the heart valve 301. In one example, the sensor 300 includes, but is not limited to a strain gauge, piezo-electric element, piezo-resistive element or the like. A valve leaflet 306 is coupled with the strut 302 and rotates at least a portion of the strut 302 during opening and closing of the heart valve 301. As the valve leaflet 306 opens and closes the sensor 300 is deflected. In another example, the deflection is measured, such as to obtain the peak angle of the valve leaflet 306 relative to the valve ring 304. The measurement of the valve leaflet 306 peak angle provides an indication of the efficiency of the heart contraction (i.e., the greater the peak angle the stronger the contraction), and is useful in determining appropriate pacing or other therapy by the implantable medical device 102, such as in a closed-loop system in which the therapy is controlled so as to maximize the measured peak angle. In yet another example, the angle measurement of the valve leaflet 306 is useful in determining the appropriate type or amount of drug to dispense by the implantable medical device 102.

In another example, the measurement of the valve leaflet 306 peak angle is performed over time. In still another example, one or more mathematical functions, such as derivatives, integrals, approximations of the same or the like are performed on the function of the valve leaflet 306 angle with respect to time. Optionally, integrating the valve leaflet angle with respect to time over a cardiac cycle provides an indication of the volume of blood flow through the valve ring 304, because the ring 304 has a consistent size and shape. In yet another example, blood flow volume is another measurement used in determining the onset of an event, changing of a condition or the like, either in addition to or in place of peak angle of the leaflet. Where the peak angle of the valve deflection does not meet a specified threshold, as described above in FIG. 2, therapy is provided (e.g., by the therapy module 220), in one example. Optionally, the heart valve 301 includes one or more electrodes 308 adapted to provide at least one of pacing and defibrillation therapy to the heart 111 (FIGS. 1A-D). For instance, the electrodes 308 extend around at least a portion of the heart valve 310 to provide defibrillation therapy. In another example, the electrodes 308 are adapted to sense one or more intrinsic cardiac signals, such as for use by the implantable medical device 102 for at least one of pacing, defibrillation, resynchronization, dispensing of drugs or the like. The heart valve 301 provides a compact device that consolidates the function of the replacement heart valve 301 with at least one of one or more sensors (e.g., sensors 300, electrodes 308 or the like) for hemodynamic parameters and/or intrinsic cardiac signals and one or more electrodes for providing therapy as described above. Additionally, the heart valve 301 (including any integral sensors 300, electrodes 308 or the like) is implantable in the heart 111 (FIGS. 1A-D) in a single procedure and eliminates the need for multiple procedures to install a heart valve, separate lead system or the like. Further, in yet another example, the heart valve 301 is installed in the left side of the heart. Where the heart valve 301 includes one or more electrodes 308 for sensing intrinsic cardiac signals, installing the valve 301 in the heart 111 avoids difficult navigation of the coronary sinus vasculature near the left side of the heart 111 required with most lead systems, and overcomes the difficulty of introducing a chronic electrode directly into the left side heart chambers of existing chronic intravascular lead systems.

Figure 4A:
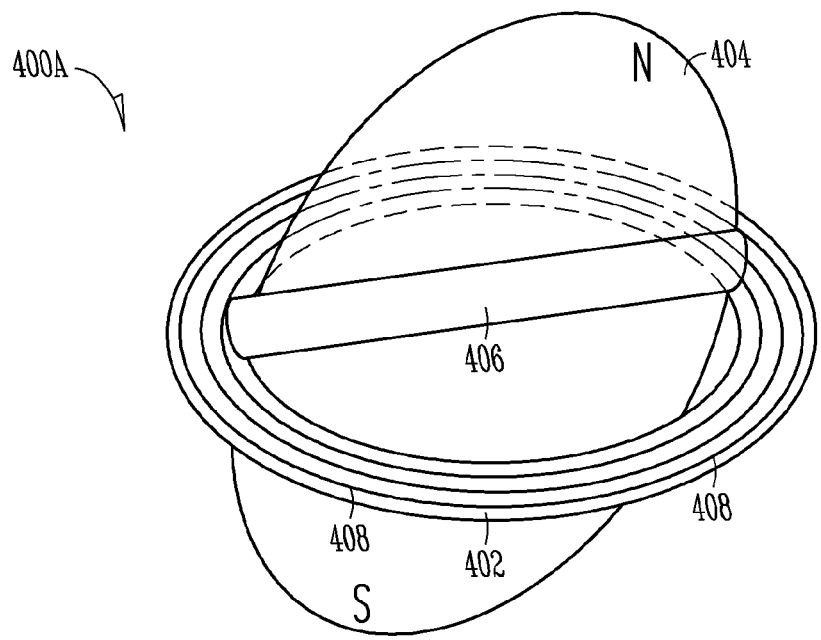
FIG. 4A is a perspective view of another example of a heart valve with a sensor for measuring at least a hemodynamic parameter.

FIGS. 4A, B show other examples of heart valves 400A, B. The heart valve 400A includes a valve ring 402, and a valve leaflet 404 rotatably coupled with the valve ring 402 by a strut 406. As shown in FIG. 4A, the valve ring 402 includes at least one coil 408 therein extending through at least a portion of the ring 402. The valve leaflet 404 is magnetized (See FIG. 4A showing North and South poles). Movement of the magnetized valve leaflet 404 with respect to the coil 408 produces a measurable potential across the coil 408. The potential corresponds with the flux variation subsequent to the change in angle and rate of change in the angle of the valve leaflet 404 with respect to the valve ring 402. As described above, the measurement of the valve leaflet 404 peak angle provides an indication of the efficiency of the heart contraction (i.e., the greater the angle the stronger the contraction), and is useful in determining appropriate electrical or other therapy by the implantable medical device 102 (FIGS. 1A-D). Additionally, the valve leaflet angle is measurable over time to obtain information about volume of blood flow, as previously described.

Figure 4B:
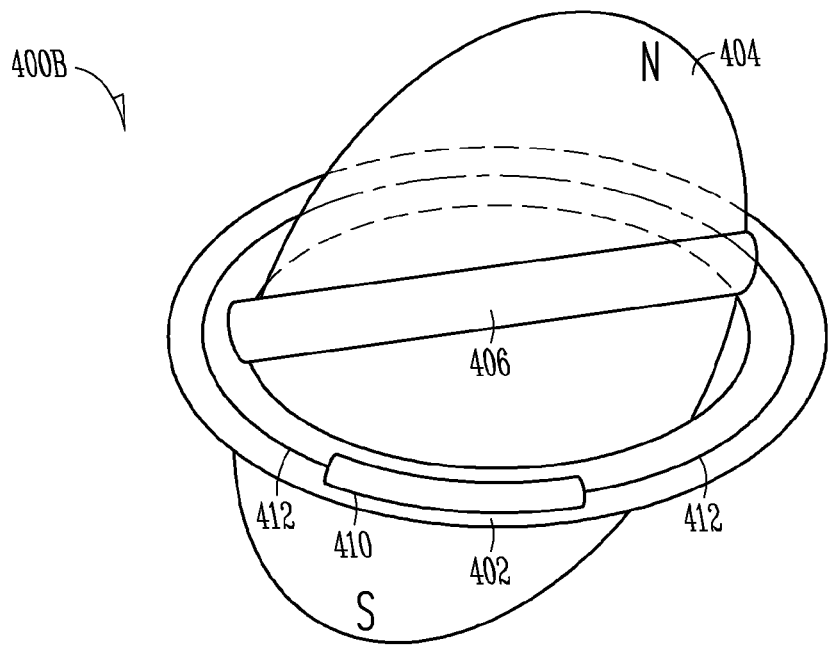
FIG. 4B is a perspective view of another example of a heart valve with a sensor for measuring at least a hemodynamic parameter.

Referring now to the heart valve 400B shown in FIG. 4B, the magnetized valve leaflet 404 and a conductive film 410 extending through a portion of the valve ring 402 or the like are used as a Hall Effect sensor to measure the angle of the valve leaflet 404. The conductive film 410 is in a closed circuit 412 with current flowing through the film 410. Changes in the current flow through the conductive film 410 occur as the magnetized leaflet 404 moves with respect to the valve ring 402. The changes in current flow are measured and correspond with the angle of the valve leaflet 404. In a similar manner to the heart valve sensor shown in FIG. 4A, the Hall Effect sensor shown in FIG. 4B provides information used to determine appropriate electrical, drug or other therapy from the implantable medical device 102.

Figure 5:
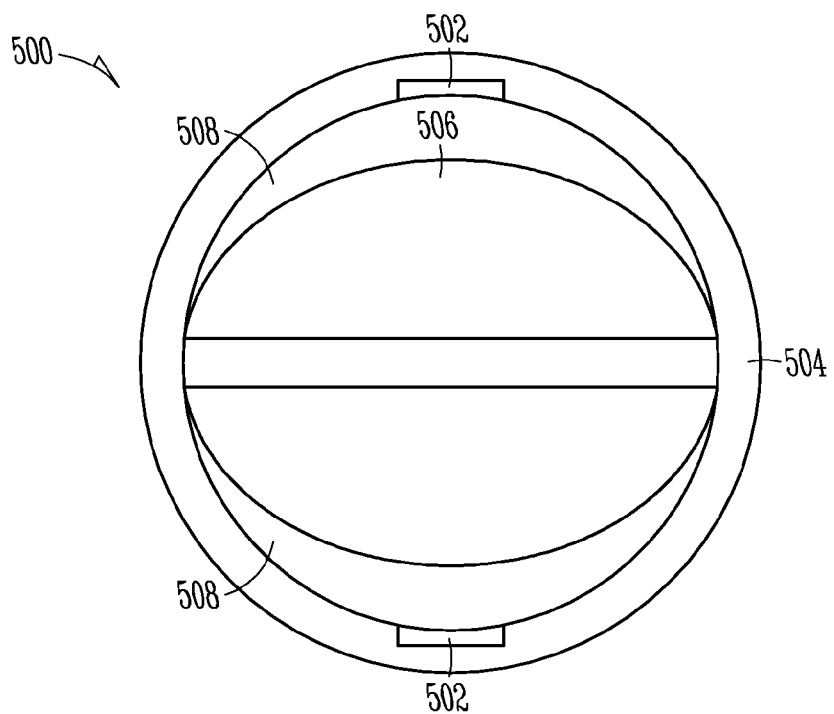
FIG. 5 is a top view of yet another example of a heart valve with a sensor for measuring at least a hemodynamic parameter.

Referring now to FIG. 5, a heart valve 500 is shown including at least one sensor 502 in a valve ring 504, such as for measuring a hemodynamic parameter (e.g., blood flow velocity). The valve leaflet 506 is shown in a partially open position. In one example, the sensor 502 includes an ultrasound generator and ultrasound detector (for instance, a piezo-electric element) that transmits ultrasonic pulses into blood flow and measures the characteristics of the pulse, such as Doppler Shift, as the ultrasound pulse reflects off the blood cells in the flow. In another example, the heart valve 500 includes a plurality of sensors 502 located around the valve ring 504. At least some of the sensors 502 act as ultrasound generators and the other sensors 502 act as ultrasound detectors. For instance, a first sensor 502 produces ultrasonic pulses, such as by applying electrical energy to a piezo-electric transducer. A second sensor 502 receives the ultrasound pulses after having reflected off of cells in the blood flow. The Doppler Shift of the pulse is measured by the valve 500 or the implantable medical device 102 and corresponds with the velocity of the blood flow. As described above, a single sensor 502 may perform both functions, in yet another example. In still another example, the sensors 502 include optical sensors (e.g., infrared sensors) that use light in a similar manner to ultrasound to measure the velocity of the blood flow. In yet another example, the sensors 502, including optical sensors, measure deflection of the valve leaflet 506 by monitoring light leakage from an optical fiber used in the sensor 502 as the valve leaflet interposes itself between the fiber and another sensor 502. In a further example, the sensors 502 include acoustic sensors that measure the acoustical scattering of sound from the valve leaflet 506 in various positions.

In another example, because the valve ring 504 has a substantially consistent orifice 508 area, measuring the velocity of blood flow through the heart valve 500 provides information used to generate the volume of blood flow through the valve. See, for instance, the flow rate equation below, where Q is the flow rate, V is the measured velocity and A is the area of the orifice 508.

$$Q = V \cdot A$$

Such information (velocity, flow rate, change in flow rate or the like) can be used by the implantable medical device 102 (FIGS. 1A-D) to assist in discriminating between fibrillation and tachycardia events in the heart 111. For instance, little or no blood velocity or volume indicates a fibrillation event. Higher blood velocity or volume indicates normal heart rhythm or tachycardia, as further described below.

Figure 6A:
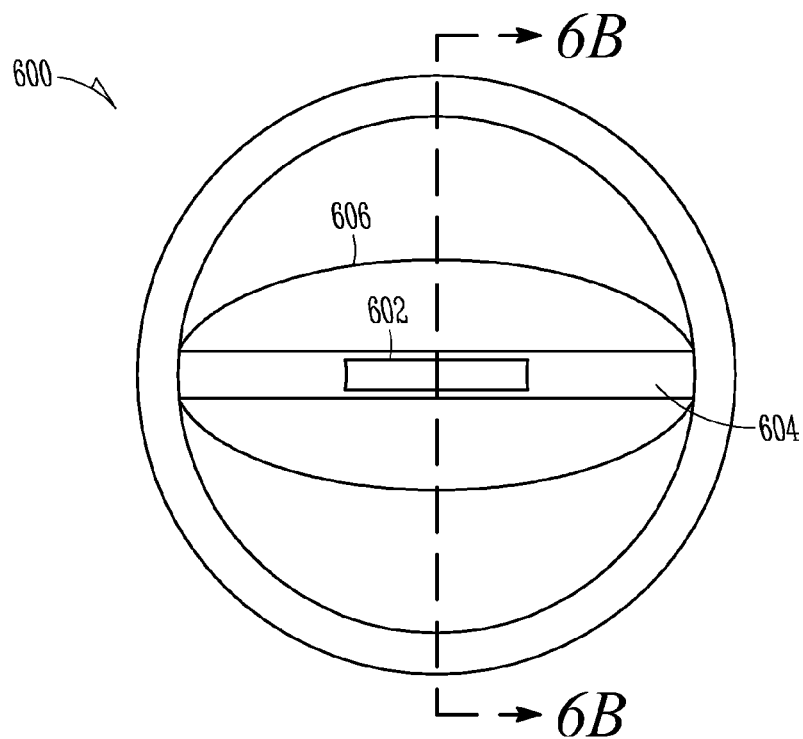
FIG. 6A is a top view of still another example of a heart valve with a sensor for measuring at least a hemodynamic parameter.

FIG. 6A shows another example of a heart valve 600 having a sensor 602 for measuring velocity and/or flow rate of a fluid, such as blood. In this example, the sensor 602 is positioned along the strut 604 and thereby in the center of the fluid flow path. The valve leaflet 606 is shown in a substantially open position. As described above, the sensor 602 includes, but is not limited to, one or more ultrasonic or optical instruments for measuring fluid velocity. The sensor 602 measures the fluid velocity by sending and receiving pulses of ultrasound or light that are reflected off of blood cells and experience a Doppler shift. In another example, multiple sensors 602 are positioned along the strut 604, and cooperate as described above with the sensors 502 shown in FIG. 5 to measure fluid velocity or flow rate. In yet another example, the sensor 602 is configured to measure transit time of a fluid, such as blood flow, with ultrasonic pulses sent against the blood flow and with the blood flow. The difference in travel time is measured and the velocity and/or flow rate is derived from that measurement.

Figure 6B:
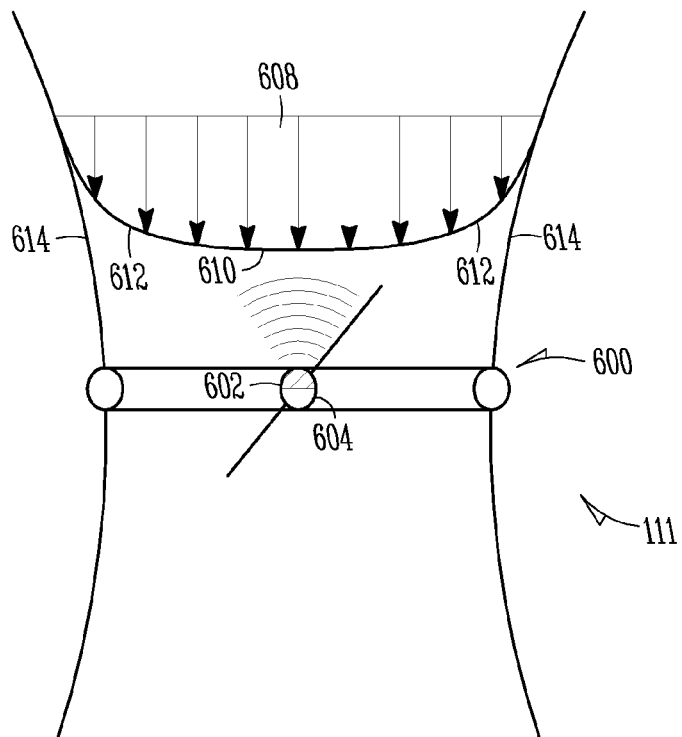
FIG. 6B is a cross-sectional view of the heart valve of FIG. 6A, taken along the section line 6B-6B.

Referring now to FIG. 6B, a cross section of the heart valve 600 taken along line 6B-6B is shown in an installed position within the heart 111. As shown, the sensor 602 is substantially pointing against the flow distribution 608. In another example, the sensor 602 is pointed in a direction with the flow distribution 608. The flow distribution 608 generally includes a laminar flow portion 610 extending over a large majority of the distribution and a turbulent flow portion 612 near the edges of the distribution (e.g., along the sidewalls 614 adjacent the valve 600). The laminar flow portion 610 generally has the highest velocities of the fluid flow (shown by the relative height of the arrows) because the laminar flow is remote from the sidewalls 614. The smaller turbulent flow portion 612 generally has lower velocity because of the drag imparted to the fluid by the sidewalls 614. Because the sensor 602 is positioned along the strut 604, the sensor 602 is able to make accurate readings of fluid velocity by measuring the velocity of the laminar portion 610 of the distribution 608. Sensors pointing into or out of the turbulent flow portion 612 can be affected by the relatively lower velocities of the turbulent flow portion 612 and thereby provide readings that are lower than the actual velocity of the majority of the fluid flow (e.g., laminar flow portion 610). Additionally, the sensor 602 is aligned with the fluid flow path (e.g., parallel) and thereby no adjustments are needed in calculating the fluid velocity because of relative angles between the fluid flow and the sensor orientation.

Figure 7:
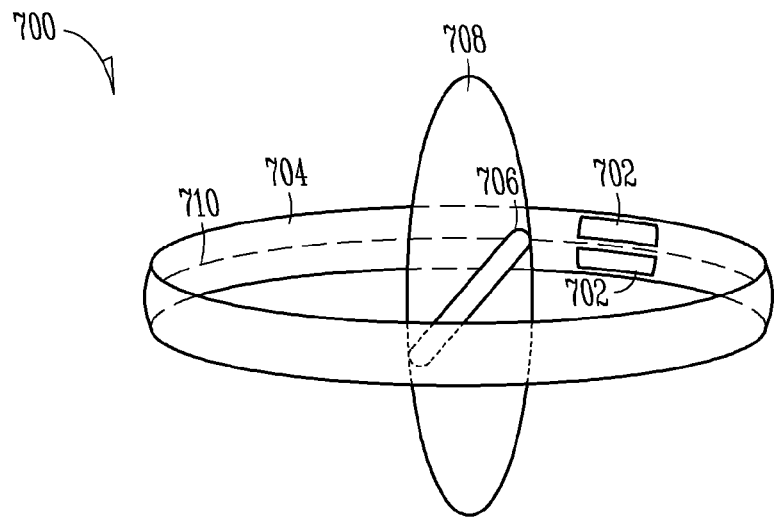
FIG. 7 is a perspective view of a further example of a heart valve with a sensor for measuring at least a hemodynamic parameter.

FIG. 7 shows yet another example of a heart valve 700 including at least one sensor 702, a valve ring 704, a strut 706 and a valve leaflet 708 coupled with the strut 706 and rotatably coupled with the valve ring 704. The sensor 702 includes a pressure transducer adapted to measure pressure in a chamber or vessel of the heart 111 (FIGS. 1A-D). As shown in FIG. 7, the heart valve 700 includes two pressure sensors 702 positioned on either side of a parting line 710. In one example, the parting line 710 is a valve leaflet seat that receives the valve leaflet 708 when the leaflet 708 is in a closed position. In another example, the sensors 702 include, but are not limited to, one or more pressure sensing diaphragms, piezoelectric elements, piezo-resistive elements or the like. The sensors 702, in yet another example, are adapted to measure the pressure in a fluid flow (e.g., blood flow). In still another example, the sensors 702 measure the pressures in two chambers of the heart. For instance, when the valve leaflet 708 is closed, the pressure sensor 702 above the parting line 710 measures the pressure in one of the right atrium and the left atrium, and the pressure sensor 702 below the parting line 710 measures the pressure in one of the right ventricle and the left ventricle, respectively (See FIGS. 1A, B). Optionally, the sensors 702 measure pressures in a chamber of the heart (e.g., the right or left ventricle), and a vessel, such as the pulmonary artery or the aorta, as shown in FIGS. 1C, D.

As described below, pressure measurements can be used to assist in detecting an event (e.g., bradycardia, tachycardia, fibrillation or the like). The heart valve 700 consolidates the pressure sensors 702 with the valve 700. This provides a convenient chronic intracardiac pressure measurement without requiring a separate implanted chronic intracardiac pressure sensor. Pressure readings of the otherwise difficult to reach left side are easily obtained by the heart valve 700 and relayed to the implantable medical device 102, such as for use in providing pacing therapy, resynchronization therapy, defibrillation therapy, drug dispensing therapy or the like.

Figure 8:
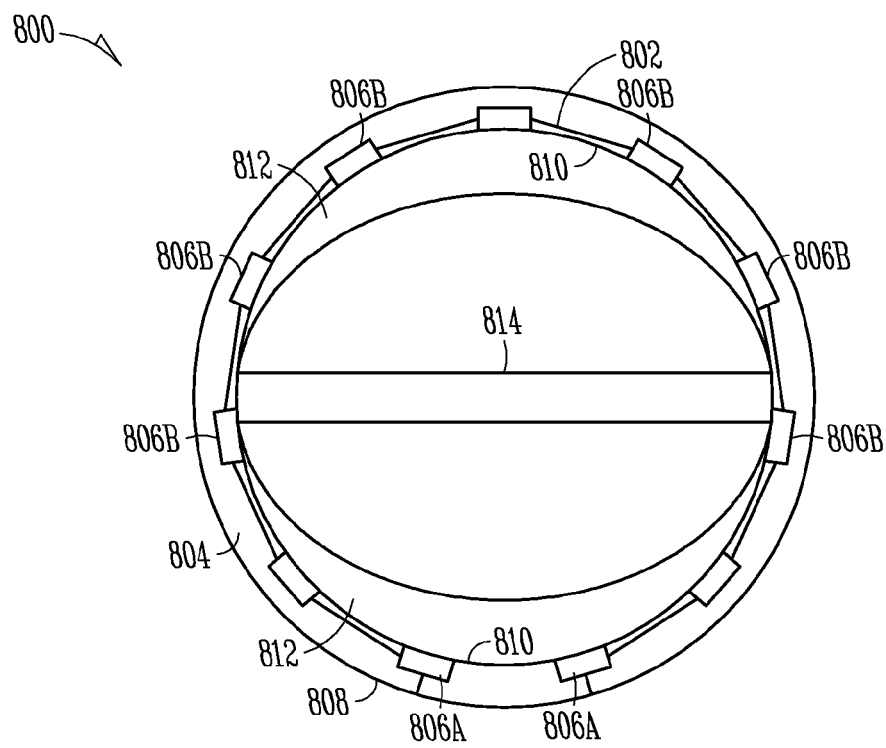
FIG. 8 is a perspective view of an additional example of a heart valve with a sensor for measuring at least a hemodynamic parameter.

FIG. 8 is still another example of a heart valve 800 including a temperature sensor 802 positioned within a valve ring 804. The temperature sensor 802, in one example, includes, but is not limited to, a thermocouple having reference nodes 806A electrically coupled with measurement nodes 806B in a closed circuit. The references nodes 806A are positioned adjacent to an exterior 808 of the valve ring 804. The measurement nodes 806B are positioned adjacent to an interior 810 of the valve ring 804, and are adapted to measure the temperature of a fluid flow (e.g., blood flow) through the valve orifice 812. The reference nodes 806A, in another example, use the body temperature (e.g., 98.6 degrees Fahrenheit) as the reference temperature. Any difference between the temperature of the fluid flow and the reference temperature is converted into a proportional electrical signal in the circuit defined by the reference and measurement nodes 806A, B. This signal is measured and used to determine a temperature of the fluid flow. In yet another example, the measurement nodes 806B are positioned along a strut 814, and otherwise similarly coupled with the references nodes 806A, as described above. In an additional example, the temperature sensor 802 includes a thermistor, and the change in potential across the resistor due to temperature is measured and converted into a temperature of the fluid flow. Temperature measurements of the fluid flow are useful for assessing cardiac efficiency or condition. In one example, changes in temperature are used in assessing cardiac pacing effectiveness as well as predicting cardiac decompensation events. Cardiac pacing parameters are automatically modulated according to temperature measurements to optimize cardiac efficiency, in another example, as a feedback mechanism. Temperature is used in assessing inflammation or infections within the heart, in still another example. For instance, medical staff is alerted to abnormal changes in temperature resulting in medical therapy (e.g., medication, further examination or the like).

In another example, the thermal output of the heart is estimated using sensors placed to observe the difference between the blood inflow and outflow temperatures. The sensors include, for instance, thermistors, thermocouples, semiconductor junctions or similar devices. The sensed locations include, but are not limited to, right atrium, right ventricle, left atrium, left ventricle, aortic valve, aortic outflow tract, mitral valve, tricuspid valve, pulmonic valve, coronary sinus, coronary veins or similar anatomic locations adjacent or containing blood flow with intimate contact to the myocardium. In one example, the sensors are located in one or more heart valves, as described herein. One arrangement for observing cardiac thermal output includes a differential temperature measurement taken from the aortic valve and the coronary sinus locations. This flow is in intimate contact with the myocardium and has sufficient transit time to communicate the heat from the tissue to the blood. The power dissipated as heat is proportional to the coronary blood flow multiplied by the difference of coronary sinus and aortic outflow temperatures. In one example, at least one of an estimate of the coronary blood flow or measurements from a flow sensor (e.g., as described herein) are used in the calculation.

The efficiency of the heart is proportional to the mean pressure of the aortic outflow tract multiplied by the cardiac output all divided by the power dissipated as heat in the muscle. The pressure of the outflow is measured, in another example, with pressure sensors included in the heart valve, as shown for instance, in FIG. 7. Multiple correction factors are included in the calculations, in yet another example, for the refinement of this measurement. The cooling effect of blood returning from the pulmonary veins is optionally included in the heat calculation if sensors are positioned in the left atrium or on or near the mitral valve. The temperature difference between right and left heart inflow and outflow streams is included in the heat calculation using the total cardiac output for net heat flux and the result used for a correction factor, in still another example. The work done on the pulmonary circuit is substantially less than that on the systemic circuit. A pressure sensor in the pulmonic outflow tract provides the needed information to calculate the pulmonic work and the result is used to increase the accuracy of the system.

In still another example, a system of sensors for estimating cardiac efficiency measures the heat transferred to the primary right or left heart flows, for instance, with heart valves including sensors to measure temperature in the right and left sides of the heart (described above). This system is implemented with a minimum of sensors while providing an estimation of cardiac efficiency based solely on heat transfer measurements.

Figure 9:
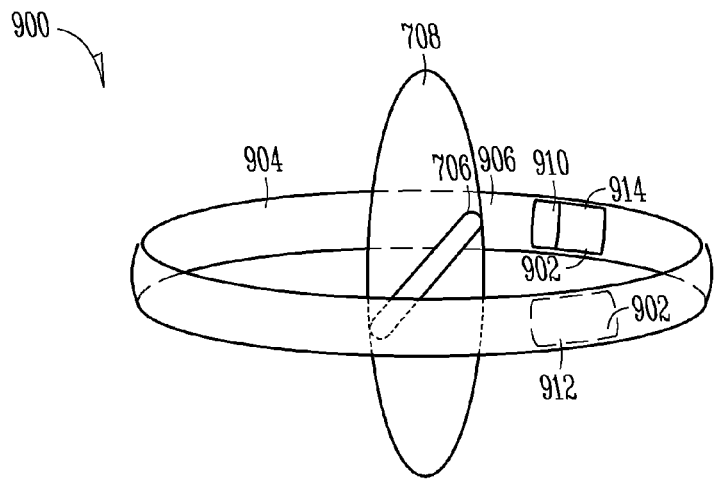
FIG. 9 is a perspective view of an additional example of a heart valve with a sensor for measuring at least a hemodynamic parameter.

Referring now to FIG. 9, another example of a heart valve 900 is shown including a chemical sensor 902. Examples of chemical sensors are described in co-pending applications, such as Kane et al. U.S. patent application Ser. No. 11/383, 933 entitled Implantable Medical Device with Chemical Sensor and Related Methods, and Kane et al. U.S. patent application Ser. No. 11/383,926 entitled Implantable Medical Device with Chemical Sensor and Related Methods, both of which are incorporated herein by reference in their entirety, including their description of chemical sensors. As shown, the chemical sensor 902 is coupled along the valve ring 904. In yet another example, the chemical sensor 902 is coupled along at least one of the strut 906 and the valve leaflet 908. The chemical sensor 902 is adapted to measure at least one of the following, including, but not limited to, potassium, oxygen, pH, creatinine, brain natriuretic peptide (BNP), lactic acid, nitric oxide or the like. At least one of these chemicals is measured and used by the implantable medical device 102 (FIGS. 1A-D), such as to develop pacing, resynchronization, defibrillation or drug dispensing therapies. Data regarding chemicals used for therapy or for diagnostic purposes may be detected by sensor 902 and provided to the implantable medical device 102 storage module 212 (FIG. 2), such as for later use by a physician, for instance through the external system 106 (FIG. 1A, B).

In one example, the chemical sensor 902 includes, but is not limited to an optical light emitting and detecting sensor that measures ion and/or analyte concentrations in a fluid flow (e.g., blood flow) to determine the presence and concentration of particular chemicals. The chemical sensor 902 includes a sensing element 910 adapted to translate analyte concentrations into variable color responses in one or more chromophore materials. The sensor 902 also includes an optical excitation module 912 integrated with the sensing element 910. The excitation module 912 is adapted to illuminate the sensing element 910 and produce an optical return signal that is responsive to analyte concentration. The sensor 902 also includes an optical detection module 914 integrated with the sensing element 910. The detection module 914 is adapted to monitor the intensity of the optical return signal to determine analyte concentration in interstitial fluid or plasma.

The sensing element 910 includes a fluorescent indicator and the optical return signal includes an analyte dependent fluorescent return signal, in some examples. According to various examples, the sensing element 910 includes a colorimetric indicator and the optical return signal includes an analyte dependent reflectance signal. In one example, the detection module 914 includes a charge-coupled device (CCD) detector. The detection module 914 includes a photo-diode detector, in another example.

The excitation module 912 includes a light-emitting diode (LED) in one example. The excitation module 912 includes one or more LEDs coupled with one or more bandpass filters, each of the LED-filter combinations emitting at a different center frequency, in another example. According to yet another example, the LEDs operate at different center-frequencies, sequentially turning on and off during a measurement, illuminating the sensing element 914. As multiple different center-frequency measurements are made sequentially, a single unfiltered detector can be used. Another implementation may use one or more laser diodes tuned to different wavelengths as illumination sources.

Another example of the chemical sensor 902 includes a reflectance-based or transmittance-based chemical sensing system. According to the reflectance-based example, the detection module 914 is on the same side of the sensing element as the excitation module 912, and the detection module 914 is adapted to monitor the intensity of the excitation light diffusely reflected off of the chemical sensor 902 or fluorescent return from the chemical sensor 902 to determine chemical analyte concentration. According to the transmittance-based example, the detection module 914 is opposite from the excitation module 912, and the detection module 914 is adapted to monitor the intensity of the excitation light transmitted from the excitation module 912 to determine chemical analyte concentration. Sensing may be directed at a specific ion or a plurality of different ions. Examples of ions that can be sensed include, but are not limited to potassium, sodium, chloride, calcium, pH and hydronium. In addition, embodiments include integrated sensors adapted to sense not only concentrations of ions, but other analytes of interest such as glucose, creatinine, lactate, urea, brain natriuretic peptide (BNP), nitric-oxide and cardiac-specific troponin, for example. Sensor embodiments may be adapted to sense an ion, multiple ions, an analyte of interest, multiple analytes of interest, or a combination thereof. According to other examples, the chemical sensor 902 includes a sensor selected from the group consisting of an electro-chemical sensor, colorimetric sensor, a fluorescent sensor and a near-infrared sensor.

Figure 10A:
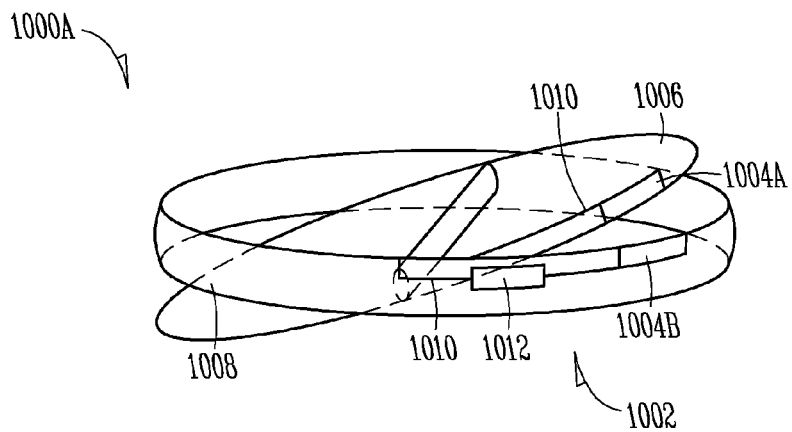
FIG. 10A is a perspective view of an example of a heart valve including an opened and closed valve indicating circuit.

FIG. 10A shows another example of a heart valve 1000A including a sensor 1002 having first and second contacts 1004A, B that indicate whether the valve leaflet 1006 is in an open or closed position. As shown, the first contact 1004A is located within a portion of the valve leaflet 1006 and is positioned to engage the second contact 1004B, in the valve ring 1008, when the leaflet 1006 is in the closed position. The first and second contacts 1004A, B are electrically coupled by a conductor 1010 extending through a portion of the valve leaflet 1006. When the valve leaflet 1006 is in the closed position a closed circuit is formed. The sensor 1002 includes a node 1012, and in one example, the node 1012 transmits the status of the valve leaflet 1006 to the implantable medical device 102 (FIGS. 1A-D). As described above, the implantable medical device 102 includes a storage module 212 that retains information about the opening and closing of the heart valve 1000A, in another example. In yet another example, the implantable medical device 102 records the time spans the heart valve 1000A is open and closed, and uses the information for modulating a therapy, such as pacing, resynchronization, defibrillation, drug dispensing or the like.

Figure 10B:
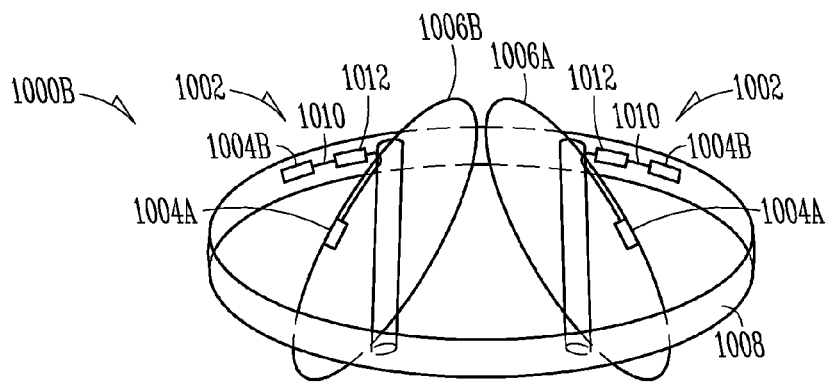
FIG. 10B is a perspective view of an example of a double leaflet heart valve including an opened and closed valve indicating circuit.

FIG. 10B shows another example of a heart valve 1000B including sensors 1002 that indicate whether the valve leaflets 1006A, B are in an open or closed position. The heart valve 1000B is similar in at least some respects to the heart valve 1000A, described above. For instance, each leaflet 1006A, B includes a first contact 1004A, and the first contact is positioned to engage a corresponding second contact 1004B, in the valve ring 1008, when the leaflet 1006A, B is in the closed position. The first and second contacts 1004A, B are electrically coupled by conductors 1010 extending through portions of the valve leaflets 1006A, B. When the valve leaflets 1006A, B are in the closed position closed circuits are formed. The sensor 1002 includes a node 1012, and in one example, the node 1012 transmits the status of the valve leaflets 1006A, B to the implantable medical device 102 (FIGS. 1A-D). Providing contacts 1004A, B on both of the leaflets 1006A, B allows for status monitoring of both leaflets 1006A, B (e.g., opening, closing, failure of a leaflet or the like) Optionally, a single set of contacts 1004A, B are provided on one of the leaflets 1006A, B. In still another option, physical contacts are avoided by using low current resistive sensing, capacitive sensing, optical sensing, Hall Effect sensing devices or the like to obtain the valve leaflet position without touching metal components. Additionally, any of the sensors described herein are usable with the heart valve 1000B having double leaflets 1006A, B, or a heart valve having a plurality of leaflets (e.g., two or more leaflets). Further, while most of the Figures have been drawn with circular valve leaflets for ease of understanding, the principles and techniques described herein apply to other moving valve configurations such as the common bi-leaflet semi-lunar designs popularly employed by physicians. These principles can be adapted to valves constructed from tissue sources such as bovine, porcine, or homologous tissue donors. Similarly, these principles can be applied to hybrid designs that use combinations of construction materials and techniques.

Figure 11:
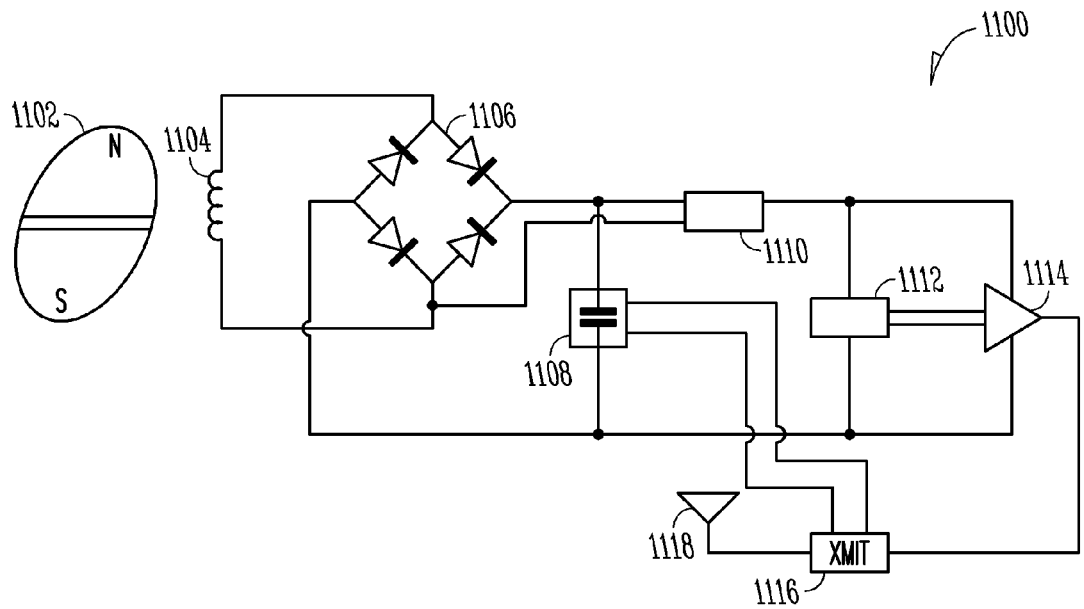
FIG. 11 is a schematic diagram of one example of a heart valve with a circuit that harvests energy and detects one or more physiological parameters.

FIG. 11 is a schematic diagram showing one example of a heart valve 1100 and circuit diagram for the same. As shown, the heart valve 1100 includes a magnetized heart valve leaflet 1102 having north and south poles. The heart valve ring includes an electromagnetic coil 1104 coupled with a rectifier 1106. A similar example is shown in FIG. 4. Movement of the heart valve 1100, for instance during each opening and closing action for a heart beat creates a current in the electromagnetic coil 1104. The current passes through the rectifier 1106 and is retained in a storage medium, such as a capacitor 1108. In another example, the heart valve 1100 includes a voltage regulator 1110 that controls the output of the coil 1104 and the leaflet 1102. Where the heart valve 1100 is separated from the implantable medical device 102 (FIGS. 1A-D) the magnetized leaflet 1102 and coil 1104 cooperate to produce electricity sufficient for the valve 1100 to operate (e.g., sense at least one physiological parameter, transmit measurements or the like). In yet another example, the heart valve 1100 is powered by another energy source such as power source 200 (FIG. 2). For instance, the power source 200 includes a battery, an induction coil coupled with a corresponding coil in at least one of the implantable medical device 102, external system 106 (FIGS. 1A, B) or the like.

Referring again to FIG. 11, a sensor 1112 measures a physiological parameter (e.g., hemodynamic characteristic, temperature, chemical, intrinsic cardiac signals or the like) and uses energy generated by the leaflet 1102 and coil 1104 (by pumping of the heart), in one example. The measurements of the sensor 1112 are optionally sent through a pre-amplifier 1114 that is similarly powered by the energy obtained through the pumping action of the heart on the valve 1100. In another example, the measurements are transmitted to at least one of the implantable medical device 102, the external system 106 or the like by the transmitter 1116 and antennae 1118. As described above, in yet another example, the transmitter 1116 operates through energy obtained by the valve leaflet 1102 and the coil 1104. Optionally, the transmitter 1116 and antenna 1118 include, but are not limited to electrodes, such as the electrodes 308 described above (e.g., pacing and/or defibrillation electrodes). In another option, the transmitter 1116 includes transducers (e.g., sensors 502, 602 or the like) adapted to sense one or more hemodynamic or other parameters and transmit ultrasound signals with such information to the implantable medical device 102 (FIGS. 1A-D).

The heart valve 1100, in another example, senses for the physiological parameter, transmits the measurement or the like intermittently as enough energy is obtained by the storage element (e.g., capacitor 1108). For instance, when the capacitor 1108 discharges (after storing a specified amount of energy) the sensor 1112 measures the physiological parameter, the measurement is amplified and then transmitted. In yet another example, the heart valve 1100 collects a plurality of measurements and stores the measurements until enough energy is retained in the capacitor to transmit the measurements. Optionally, the heart valve 1100 includes a microprocessor that controls the function of at least one of the sensor 1112, transmitter 1116 or the like.

Referring now to FIG. 3, in one example, the sensors 300 coupled between the valve leaflet 306 and the valve ring 304 include one or more piezo-electric elements. Movement of the valve leaflet 306 causes corresponding deflection of the piezo-electric elements to obtain electricity. In a similar manner described above, the piezo-electric sensor elements provide power for sensing, amplifying and transmitting signals to at least one of the implantable medical device 102, external system or the like.

Figure 12:
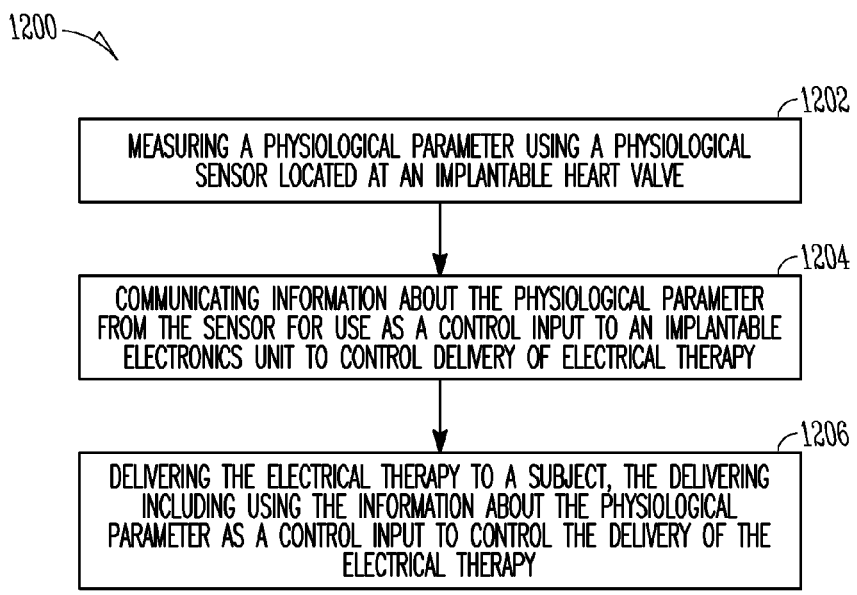
FIG. 12 is a block diagram showing one example of an event detection method.

FIG. 12 is an example of a flow chart showing one example of a cardiac management method 1200. At 1202, a physiological parameter (e.g., hemodynamic characteristic, temperature, chemical, intrinsic cardiac signal or the like) is measured using a physiological sensor located at an implantable heart valve, such as one or more of including the heart valves shown in FIGS. 1A-11. At 1204, information about the physiological parameter, such as a measurement, is communicated from the sensor in the heart valve, such as to an implantable electronics unit, for instance, the implantable medical device 102. The information is used as a control input to control delivery of electrical or other therapy, in one example. In another example, the information is used as a control input to control delivery of pacing therapy, resynchronization therapy, defibrillation therapy or drug dispensation. Optionally, the implantable electronics unit is physically separated from the heart valve and remote therefrom. At 1206, the method 1200 includes delivering the electrical therapy. For example, the electrical therapy is delivered through electrodes, such as electrodes 308 (FIG. 3) in the heart valve. In yet another example, the therapy is delivered through leads separate from the heart valve. Delivery of the therapy is regulated by the physiological parameter information transmitted from the heart valve to the implantable medical device.

Several variations for the method 1200 follow. In one example, measuring the physiological parameter includes measuring an intrinsic electrical cardiac signal (e.g., P-wave, T-wave, S-T segment, QRS-complex or the like), the relationship between subsequent or successive ECG signals, such as morphology and intervals, or the like. Additionally, intervals, morphology or the like between individual intrinsic electrical cardiac signal features (e.g., P-wave, T-wave, S-T segment, QRS-complex or the like) are measured, optionally. In another example, measuring the physiologic parameter includes measuring at least one hemodynamic parameter, such as blood flow, blood pressure, heart valve deflection, heart valve deflection rate or the like. Measuring the heart valve deflection includes measuring the valve leaflet angle, in yet another example.

In another example, the method 1200 includes detecting an event, such as tachyarrhythmia, bradyarrhythmia and the like (e.g., by measuring the intrinsic electrical cardiac signal and measuring at least one hemodynamic parameter). The event is classified as a first tachyarrhythmia type if the measured hemodynamic parameter indicates inadequate cardiac output. The event is classified as a second tachyarrhythmia type if the measured hemodynamic parameter indicates adequate cardiac output. In yet another example, measuring the hemodynamic parameter indicates whether blood continues to adequately flow through the heart, or if the tachyarrhythmia is serious enough there is inadequate blood flow. In still another example, a first anti-tachyarrhythmia therapy (e.g., anti-tachyarrhythmia pacing therapy) is delivered in response to a detected tachyarrhythmia of the first tachyarrhythmia type. A second anti-tachyarrhythmia therapy (e.g., defibrillation therapy) is delivered in response to a detected tachyarrhythmia of the second tachyarrhythmia type. Additional accuracy is provided by comparing the intrinsic electrical cardiac measurement and the hemodynamic measurement with respective thresholds. For instance, inappropriate therapy, such as defibrillation shocking, is avoided when the hemodynamic measurement (e.g., blood flow, blood velocity, pressure or the like) exceeds the threshold indicating there is still flow through the heart, while the electrical cardiac measurement alone may indicate a fibrillation event. Therefore, appropriate antitachycardia pacing is provided, in another example, until the condition stabilizes or the hemodynamic parameter also indicates fibrillation (e.g., blood flow, velocity, pressure or the like fall below the hemodynamic threshold). Optionally, a condition, such as bradycardia is detected and treated in a similar manner (i.e., by measuring intrinsic electrical cardiac signals and at least one hemodynamic parameter and adjusting or providing pacing therapy). A system including the implantable heart valve having hemodynamic sensors as described above, along with an implantable medical device (e.g., a pulse generator) that uses the measurements of the hemodynamic sensors along with intrinsic electrical cardiac measurements is thereby able to discriminate more accurately between conditions and provide the more appropriate therapy for the particular condition.

Optionally, the method 1200 includes changing a pacing site or inter electrode timing based on the measurements of the physiological parameter (e.g., hemodynamic parameter, intrinsic electrical cardiac signal or the like). For instance, different electrodes at positions along a lead assembly (e.g., electrodes 105 on lead assembly 104) or on the heart valve are used to deliver therapy to various heart locations based on the physiological parameters measured by the heart valve. Altering the pacing site or interelectrode timing based on these measurements resynchronizes the spatial nature of a heart contraction and thereby increases its output.

In yet another example, the method 1200 includes obtaining energy by movement of a portion of the valve. The energy is optionally stored in the heart valve. The method 1200 further includes using the energy, such as for the measuring functions (e.g., measuring at least one physiological parameter), communicating information, including measurements, to at least one of an implantable medical device, external system or the like. In one example, obtaining energy includes using blood flow for deflecting a piezo-electric element coupled between a valve ring and a valve leaflet, as described above in FIG. 3. In another example, obtaining energy includes moving a magnetic portion of the valve with respect to a coil in a valve ring, for instance, as shown in FIG. 4.

In still another example, the method 1200 includes adjusting a delay between electrical pulses delivered to the same or different heart chambers using the information about the physiological parameter as a control input. In one example, measuring the physiological parameter includes measuring a duration for which the heart valve is open, and the delay is adjusted so as to generally increase the measured duration for which the heart valve is open. Optionally, adjusting the delay is performed as a feedback loop with the electrical pulse therapy to adjust the heart output. Adjusting the delay between pulses according to measurements of the physiological parameter taken by the heart valve is performed to resynchronize the heart function (contraction or filling between the left and right sides) and thereby optimize the performance and output of the heart. In another example, the delay is adjusted to generally minimize a time interval between: (1) an electrical pulse delivered to one of the right and left ventricles; and (2) an opening of the heart valve. Minimizing this time interval, for instance, adjusts the output of the ventricular contractions. In yet another example, adjusting the delay includes adjusting the atrial-ventricular delay between an electrical pulse delivered to an atrium and an electrical pulse delivered to the ventricle during the same cardiac cycle. Optionally, measuring the physiological parameter with the heart valve includes measuring a delay between an opening of a first valve and an opening of a second valve (e.g., at least one hemodynamic sensor is included in each of two replacement heart valves).

In another example, the physiological parameter measured (e.g., blood flow, valve leaflet deflection, leaflet deflection rate, valve opening duration, blood velocity, chemical presence and concentration, temperature or the like) are used as an indication of cardiac output (described above) and valve patency. For instance, sensors in the heart valve measure at least one of flow and pressure through the valve during regular heart activity and also measure regurgitation of blood (e.g., velocity, flow, pressure or the like) through the valve if the valve leaflet fails to fully close as a chamber contracts. Leaks through the valve are thereby identified and replacement of the valve performed if needed. The method 1200 further includes using the indication of cardiac output to establish a rate-responsive pacing upper rate limit. Pacing is thereby adjusted to provide the needed cardiac output without needlessly raising the pacing rate without obtaining a corresponding increase in cardiac output.

As described above, adjustment of the hemodynamic parameter can be accomplished by coordinating contractions of the chambers to obtain stronger contraction. For example, by adjusting the pacing site or the delay between electrical pulses to chambers of the heart (one or more chambers) the heart contracts in a more spatially coordinated manner to adjust at least one hemodynamic parameter, such as blood flow. In one example, the hemodynamic parameter is measured at implantable aortic and pulmonic valves, as shown in FIGS. 1C, D.

Optionally, the hemodynamic parameter is measured at implantable mitral and tricuspid valves (FIGS. 1A, B), such as to measure the efficiency of diastolic function (i.e., how efficiently the heart ventricles are filling with blood).

In an additional example, the physiological measurements taken by the heart valve are used by at least one of the implantable electronics unit (e.g., implantable medical device 102), the external system or the like for ischemia detection in the heart. For instance, measurement of a decreased blood flow with the heart valve sensors described above may indicate a myocardial infarction, which can then be more quickly treated because of the measured change in blood flow.

Figure 13:
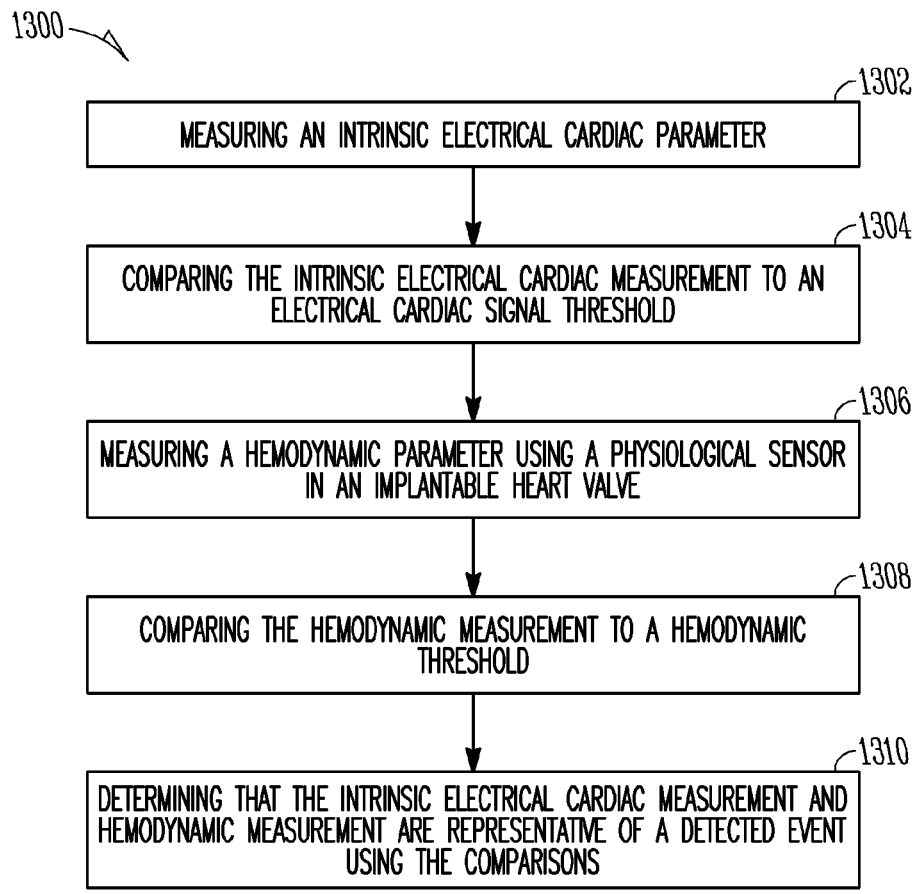
FIG. 13 is a block diagram showing one example of an event detection method.

FIG. 13 is another example of a flow chart showing an example of a cardiac management method 1300. At 1302, an intrinsic electrical cardiac parameter is measured (e.g., a QRS complex). In one example, the intrinsic electrical cardiac parameter is measured with one or more sensors on an implantable heart valve, such as with electrode 308 described above. In another example, the intrinsic electrical cardiac parameter is measured with one or more electrodes positioned along a lead or an implantable medical device (e.g., such as implantable medical device 102 shown in FIGS. 1A-D). In yet another example, the intrinsic electrical cardiac parameter is measured between an electrode at the valve and at least one of an electrode along a lead, electrode at the implantable medical device 102 or the like. By measuring between the valve and another electrode new sensing vectors are generated to measure electrical parameters across a variety of regions in the heart. As described below, optionally, pacing or defibrillation therapy is also provided along at least one of these vectors or along the lead assembly and implantable medical device 102.

At 1304, the intrinsic electrical cardiac measurement is compared with an electrical cardiac reference, such as a rate threshold, morphology template or the like. At 1306, a hemodynamic parameter is measured using a physiological sensor at the implantable heart valve, as described above. At 1308, the hemodynamic measurement is compared with a hemodynamic reference (e.g., blood flow, blood velocity, valve leaflet angle, valve opening duration, chemical presence and concentration, temperature thresholds or the like). At 1310, the method 1300 includes determining whether the intrinsic electrical cardiac measurement and hemodynamic measurement are representative of a detected event (e.g., bradycardia, tachycardia, fibrillation or the like), such as based on the comparisons of the intrinsic electrical cardiac measurement and the hemodynamic measurement. Optionally, an alert or therapy (anti-tachycardia, defibrillation, pacing, resynchronization, drug dispensing therapies or the like) are provided according to this determination. Additional accuracy is provided by comparing the intrinsic electrical cardiac measurement and the hemodynamic measurement with respective references. For instance, inappropriate therapy, such as defibrillation shocking, is avoided when the hemodynamic measurement (e.g., blood flow, blood velocity, pressure or the like) exceeds a threshold, indicating there is still adequate flow through the heart, even though the electrical cardiac measurement alone may indicate a fibrillation event. Therefore, appropriate antitachycardia pacing is provided, in another example, until the condition stabilizes or the hemodynamic parameter also indicates fibrillation (e.g., blood flow, velocity, pressure or the like fall below the hemodynamic threshold). A system including the implantable heart valve having one or more hemodynamic sensors as described above, along with an implantable medical device (e.g., a pulse generator) that uses the measurements of the hemodynamic sensors along with intrinsic electrical cardiac measurements is thereby able to discriminate more accurately between conditions and provide the best response for the particular condition.

Several variations for the method 1300 follow. In one example, determining the intrinsic electrical cardiac measurement and hemodynamic measurement are representative of a detected event includes determining the detected event is a first type of tachycardia event where the intrinsic electrical cardiac measurement (e.g., depolarization rate) exceeds the electrical cardiac threshold, and the hemodynamic measurement is above the hemodynamic threshold. In another example, determining the intrinsic electrical cardiac measurement and hemodynamic measurement are representative of a detected event includes determining the detected event is a second type of tachycardia event (e.g., fibrillation) where the intrinsic electrical cardiac measurement (e.g., depolarization rate) exceeds the electrical cardiac threshold, and the hemodynamic measurement is below the hemodynamic threshold. Distinguishing between symptomatic and non-symptomatic ventricular tachycardia is important because the appropriate type of therapy delivered by the device is specific to the type of ventricular tachycardia. Patients with symptomatic ventricular tachycardia (VT) and/or ventricular fibrillation (VF) have little to no blood perfusion. In this case a defibrillation shock is appropriate therapy. Patients with episodes of non-symptomatic VT still have adequate perfusion. In this case other therapies such as rapid or burst pacing can break the arrhythmia with less pain and danger to the patient. Patients with bradycardia or myocardial infarction may still have adequate perfusion unless these conditions degenerate or create secondary hemodynamically unstable pathologies.

In one example, low cardiac output is the result of bradycardia, myocardial infract, fibrillation or the like. Low cardiac output resulting from bradycardia is distinguishable by the presence of a low frequency periodic contraction of the heart. Around 60 beats per minute or less with low cardiac output and a distinct periodic ECG or valve sensor signal (described above) is indicative of this cause. The heart rate signal can be observed using electrodes to detect the depolarization potentials, the valve position or valve motion sensor to detect the rate of valve cycling, the flow sensor to detect the periodic rate of blood flow, or the pressure sensors to detect the periodic variation of pressures within a chamber or across a valve.

Low cardiac output from fibrillation is distinguished, in another example, by the lack of periodicity of the ECG or by the presence of dominant high frequency components in the ECG waveform. Valve motion sensors indicate incomplete or very rapid valve position variations. Pressure sensors indicate high rate pressure fluctuations with small amplitudes.

In yet another example, low cardiac output from infarct is distinguished by an elevated heart rate well above the resting rate but substantially below the 185 beat per minute associated with tachycardia. The suite of sensors described above for the detection of bradycardia and fibrillation rates will provide the data to combine with the low cardiac output signal. These data are then processed to indicate the infarct as the probable cause of low cardiac output. Another distinguishing characteristic of infarct is the change in ECG vector behavior (e.g., an elevated S-T segment). This is uniquely identifiable with a sensor equipped valve that has multiple electrodes positioned on the annulus of the valve body, as described above. The morphology and vector changes from two or more electrodes are processed (e.g., by the implantable medical device 102, external system 106 or the like) to identify the probable cause as infarct.

In still another example, the tachycardia event, such as fibrillation, is distinguished from a bradycardia condition or myocardial infarct by measuring the R-R interval, for instance, with sensors in the heart valve. Fibrillation has a measurably shorter R-R interval than bradycardia or a myocardial.

In another example, the hemodynamic threshold includes a valve leaflet angle threshold and measuring the hemodynamic parameter includes measuring a valve leaflet angle, as described above in FIGS. 3 and 4, for example. In yet another example, the hemodynamic parameter measured with the heart valve includes blood flow pressure, pressure within at least one chamber, blood velocity, rate of change of valve leaflet angle or the like.

In still another example, the method 1300 includes communicating at least one of the intrinsic electrical cardiac measurement and the hemodynamic measurement to at least one of an implantable medical device (e.g., implantable medical device 102), an external system or the like. In one example, the measurements are communicated by at least one of a lead assembly, EMF generation (e.g., through electrodes on the heart valve, described above), ultrasound (through piezoelectric and piezo-resistive elements, also described above), RF, inductive coupling, optically (e.g., with infrared light) or the like, as described above.

Figure 14:
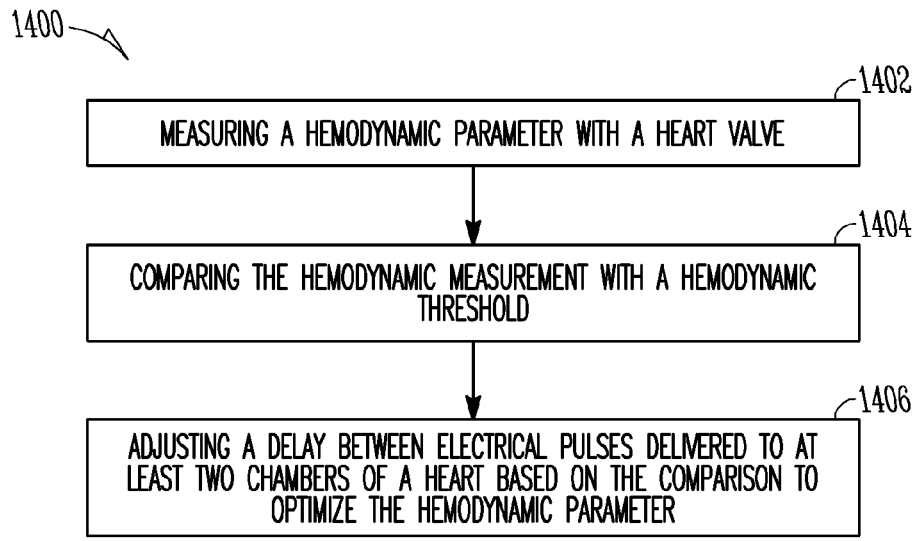
FIG. 14 is a block diagram showing one example of a cardiac resynchronization method.

FIG. 14 is an example of a flow chart showing yet another example of a cardiac management method 1400. At 1402, a hemodynamic parameter is measured using a sensor coupled with a heart valve. Examples of sensors coupled with the heart valve are described above and shown in FIGS. 2-11. At 1404, the hemodynamic measurement is compared with a corresponding hemodynamic threshold (e.g., blood flow, blood velocity, valve leaflet angle, rate of change of valve leaflet angle, valve opening duration, chemical, temperature thresholds or the like). At 1406, a delay is adjusted between electrical pulses delivered to at least one of two chambers of the heart, a single chamber of the heart (e.g., different locations within the same chamber) or the like. The delay is changed based on the comparison to adjust the hemodynamic parameter. For instance, the delay between pulses is adjusted to resynchronize the spatial nature of depolarization within a chamber and/or between chambers. In another example, the sensors of the heart valve cooperate with logic (described above) within an implantable medical device (e.g., device 102 shown in FIGS. 1A-D) to adjust pacing or resynchronization therapy in a feedback system to adjust the hemodynamic parameter. As described above, adjustment of the hemodynamic parameter is accomplished by coordinating contractions of the chambers to increase the efficiency of the heart contraction. By adjusting the delay between electrical pulses, the chambers of the heart contract in a more coordinated manner to adjust at least one hemodynamic parameter, such as blood flow. In one example, the hemodynamic parameter is measured at implantable aortic and pulmonic valves, as shown in FIGS. 1C, D. Optionally, the hemodynamic parameter is measured at implantable mitral and tricuspid valves (FIGS. 1A, B), such as to measure the efficiency of diastolic function (i.e., how efficiently the heart ventricles are filling with blood).

Several variations for the method 1400 follow. In one example, comparing the hemodynamic measurement with the hemodynamic parameter and adjusting the delay between electrical pulses is performed by an implantable medical device (e.g., device 102 shown in FIGS. 1A-D), such as a cardiac function management system.

In another example, the hemodynamic parameter measured is the duration the heart valve is open. Optionally, adjusting the delay between electrical pulses to at least two heart chambers based on the comparison of the measurement with the threshold increases the duration the heart valve is open (e.g., increases the cardiac output through the valve). In yet another example, adjusting the delay between electrical pulses to at least two heart chambers includes adjusting a delay between pulses to the left and right ventricles to minimize a delay between at least one pulse and the opening of the valve to thereby enhance, for instance, cardiac output. The valve opening and pulse substantially correspond to more efficiently expel blood through the open valve during the contraction. In still another example, the delay is adjusted between pulses to an atrium and a ventricle. In an additional example, measuring the hemodynamic parameter includes measuring a delay between the opening of a first implantable heart valve and the opening of a second implantable heart valve. As described above, the method 1400 includes changing the pacing site based on the comparison to adjust the hemodynamic parameter (e.g., blood flow, valve opening duration, valve leaflet angle or the like).

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A method comprising:
   monitoring at least two physiological parameters using respective physiological sensors located at an implantable heart valve including:
      monitoring at the heart valve an intrinsic electrical cardiac signal with an intrinsic electrical cardiac sensor located at the heart valve, and
      monitoring a hemodynamic parameter at the heart valve with a hemodynamic sensor located at the heart valve; and
   identifying a cardiac event using information about the physiological parameters from the physiological sensors at the heart valve, the identifying including:
      detecting a cardiac event using information from at least one of the intrinsic electrical cardiac signal monitoring or hemodynamic parameter monitoring, and
      classifying the cardiac event using information from one of the intrinsic electrical cardiac signal monitoring or hemodynamic parameter monitoring.

2. The method of claim 1, comprising communicating information about the physiological parameters from the physiological sensors at the heart valve to an implantable electronics unit, wherein the implantable electronics unit performs the identifying the cardiac event and controls delivery of electrical cardiac therapy in response to the classifying of the cardiac event.

3. The method of claim 1, wherein the cardiac event includes a bradyarrhythmia event and identifying the cardiac event includes:
   detecting the cardiac event with the intrinsic electrical signal monitoring at the heart valve indicating one or more of a heart rate of less than a specified threshold value or a characteristic ECG depolarization waveform, and
   classifying the cardiac event as the bradyarrhythmia event when the hemodynamic parameter monitoring at the heart valve indicates hemodynamic cardiac output below a specified hemodynamic cardiac output threshold.

4. The method of claim 3, wherein monitoring the hemodynamic parameter at the heart valve includes measuring one or more of a periodic rate of blood flow, periodic pressure variation within a chamber, or periodic pressure variation across the heart valve, and the specified output threshold for classifying the cardiac event includes one or more of a periodic blood flow rate threshold, a periodic pressure variation threshold within a chamber, or a periodic pressure variation threshold across the heart valve.

5. The method of claim 1, wherein the cardiac event includes a fibrillation event, and identifying the cardiac event includes:
   detecting the cardiac event with the hemodynamic parameter at the heart valve indicating hemodynamic cardiac output below a specified output threshold, and
   classifying the cardiac event as the fibrillation event when the intrinsic electrical signal measurement at the heart valve indicates one or more of a specified ECG wave form periodicity or an ECG high frequency component exceeding a specified high frequency threshold.

6. The method of claim 5, wherein monitoring the hemodynamic parameter at the heart valve includes measuring one or more of valve motion or pressure fluctuation, and
   the specified output threshold for detecting the cardiac event includes one or more of a valve motion threshold indicating incomplete or rapid valve position variation, or a pressure change threshold indicating small amplitude pressure fluctuations at the heart valve relative to a regular pressure fluctuation amplitude.

7. The method of claim 1, wherein the cardiac event includes an ischemia event, and identifying the cardiac event includes:
   detecting the cardiac event with the hemodynamic parameter monitoring at the heart valve indicating hemodynamic cardiac output below a specified output threshold, and
   classifying the cardiac event as the ischemia event where the intrinsic electrical signal measurement at the heart valve indicates one or more of a heart rate above a specified resting heart rate threshold and below a specified tachycardia heart rate threshold, or an elevated S-T segment above a specified S-T segment threshold.

8. The method of claim 1, comprising adjusting the hemodynamic parameter in response to the monitoring of the intrinsic electrical cardiac signal and monitoring of the hemodynamic parameter.

9. The method of claim 8, wherein adjusting the hemodynamic parameter includes:
   associating a first sequential electrical cardiac delay with a first hemodynamic parameter measurement,
   associating a second sequential electrical cardiac delay with a second hemodynamic parameter measurement, wherein the first and second sequential electrical cardiac delays are different and in sequence with each other, and the second hemodynamic parameter measurement is adjusted using the first hemodynamic parameter measurement,
   associating a third sequential electrical cardiac delay with a third hemodynamic parameter measurement, the third hemodynamic parameter measurement is less optimal than the second hemodynamic parameter measurement, and the third sequential electrical cardiac delay is different from and in sequence to the first and second sequential electrical cardiac delays,
   comparing the first, second and third hemodynamic parameter measurements, and determining whether the second hemodynamic parameter measurement is optimal, and
   adjusting an electrical pulse therapy delay to correspond with the second sequential electrical cardiac delay to adjust the hemodynamic parameter.

10. The method of claim 1, comprising determining a rate responsive pacing upper rate limit.

11. The method of claim 10, wherein determining the rate responsive pacing upper limit includes:
    associating a first sequential pacing rate with a first hemodynamic parameter measurement,
    associating a second sequential pacing rate with a second hemodynamic parameter measurement, the first and second sequential pacing rates are different and in sequence with each other, and the second hemodynamic parameter measurement is optimal relative to the first hemodynamic parameter measurement,
    associating a third sequential pacing rate with a third hemodynamic parameter measurement, the third hemodynamic parameter measurement is less optimal than the second hemodynamic parameter measurement, and the third sequential pacing rate is different from and in sequence to the first and second sequential pacing rates,
    comparing the first, second and third hemodynamic parameter measurements, and determining whether the second hemodynamic parameter measurement is optimal, and
    adjusting an electrical pacing rate to correspond with the second sequential pacing rate for use as the rate responsive pacing upper limit.

12. A method comprising:
    monitoring at least two physiological parameters using respective physiological sensors located at an implantable heart valve including:
       monitoring at the heart valve an intrinsic electrical cardiac signal with an intrinsic electrical cardiac sensor located at the heart valve, and
       monitoring a hemodynamic parameter at the heart valve with a hemodynamic sensor located at the heart valve; and
    identifying one or more cardiac events using information about the physiological parameters from the physiological sensors at the heart valve, the identifying including:
       detecting a cardiac event using information from the hemodynamic parameter monitoring at the heart valve,
       classifying the cardiac event as a first cardiac event using information from the intrinsic electrical cardiac signal monitoring at the heart valve that meets a first intrinsic electrical threshold, and
       classifying the event as a second cardiac event using information from the intrinsic electrical cardiac monitoring at the heart valve that meets a second intrinsic electrical threshold different from the first intrinsic electrical threshold.

13. The method of claim 12, wherein identifying one or more cardiac events includes:
    detecting the cardiac event including a low hemodynamic output event with the hemodynamic parameter monitoring at the heart valve,
    classifying the low hemodynamic output event as the first cardiac event including bradyarrhythmia when the intrinsic electrical cardiac signal monitoring indicates a heart rate of less than a specified threshold value,
    classifying the low hemodynamic output event as the second cardiac event including fibrillation if the intrinsic electrical cardiac signal monitoring indicates a specified ECG wave form periodicity or an ECG high frequency component exceeding a specified high frequency threshold.

14. The method of claim 12, wherein identifying one or more cardiac events includes:

detecting the cardiac event including a low hemodynamic output event with the hemodynamic parameter monitoring at the heart valve, and classifying the low hemodynamic output event as the first cardiac event including ischemia if the intrinsic electrical cardiac signal monitoring indicates a heart rate above a resting heart rate threshold and below a tachyarrhythmia heart rate threshold.

15. The method of claim 14, wherein ischemia includes myocardial infarction.

16. The method of claim 14, wherein classifying the low hemodynamic output event as the second cardiac event includes classifying the second cardiac event as one of bradyarrhythmia or tachyarrhythmia including:

classifying the second cardiac event as bradyarrhythmia where the intrinsic electrical signal monitoring indicates the heart rate is below the resting heart rate threshold, and classifying the second cardiac event as tachyarrhythmia where the intrinsic electrical signal monitoring indicates the heart rate is at or above a tachyarrhythmia heart rate threshold.

17. The method of claim 12, wherein identifying one or more cardiac events includes:

detecting the cardiac event including a low hemodynamic output event with the hemodynamic parameter monitoring at the heart valve, and classifying the low hemodynamic output event as the first cardiac event including ischemia when the intrinsic electrical cardiac monitoring indicates an elevated S-T segment relative to an S-T segment threshold.

18. The method of claim 12, wherein identifying one or more cardiac events using information about the physiological parameters from the physiological sensors at the heart valve includes:

detecting the cardiac event including a low hemodynamic output event with the hemodynamic parameter monitoring at the heart valve, and classifying the cardiac event as a first cardiac event including bradyarrhythmia when the intrinsic electrical cardiac monitoring indicates a distinct bradyarrhythmia periodic ECG signal.

19. The method of claim 12, wherein identifying one or more cardiac events with information about the physiological parameters from the physiological sensors at the heart valve includes:

detecting the cardiac event including a low hemodynamic output event using the hemodynamic parameter monitoring at the heart valve, and classifying the cardiac event as a first cardiac event including fibrillation when the intrinsic electrical cardiac monitoring indicates a specified ECG wave form periodicity threshold of an ECG wave form or an ECG high frequency component exceeding a specified high frequency threshold.

20. The method of claim 12, wherein monitoring the hemodynamic parameter at the heart valve includes one or more of monitoring a periodic rate of blood flow with a flow sensor, monitoring a valve cycling rate or monitoring pressures within one or more heart chambers.

* * * * *